(12) United States Patent
Velasco et al.

(10) Patent No.: US 7,313,442 B2
(45) Date of Patent: Dec. 25, 2007

(54) METHOD OF TREATING MOOD DISORDERS AND/OR ANXIETY DISORDERS BY BRAIN STIMULATION

(75) Inventors: Francisco Velasco, Mexico City (MX); Fiacro Jimenez, Col. Roma (MX); Marcos Velasco, Mexico City (MX); Andres M. Lozano, Toronto (CA)

(73) Assignee: Advanced Neuromodulation Systems, Inc., Plano, TX (US)

( * ) Notice: Subject to any disclaimer, the term of this patent is extended or adjusted under 35 U.S.C. 154(b) by 95 days.

(21) Appl. No.: 11/118,140

(22) Filed: Apr. 29, 2005

(65) Prior Publication Data

US 2006/0064138 A1 Mar. 23, 2006

Related U.S. Application Data

(60) Provisional application No. 60/567,332, filed on Apr. 30, 2004.

(51) Int. Cl.
*A61N 1/36* (2006.01)
(52) U.S. Cl. ............................ 607/45; 607/3; 607/117; 600/378
(58) Field of Classification Search ................ 607/2, 607/3, 45, 46, 115, 116, 117; 600/378
See application file for complete search history.

(56) References Cited

U.S. PATENT DOCUMENTS

| 3,653,385 A | 4/1972 | Burton |
| 3,731,681 A | 5/1973 | Blackshear et al. |
| 3,951,147 A | 4/1976 | Tucker et al. |
| 4,692,147 A | 9/1987 | Duggan |
| 4,772,263 A | 9/1988 | Dorman et al. |
| 4,883,057 A | 11/1989 | Broderick |
| 4,892,538 A | 1/1990 | Aebischer et al. |
| 5,119,832 A | 6/1992 | Xavier |
| 5,125,888 A | 6/1992 | Howard et al. |
| 5,263,480 A | 11/1993 | Wernicke et al. |
| 5,299,569 A | 4/1994 | Wernicke et al. |

(Continued)

FOREIGN PATENT DOCUMENTS

WO WO-0197906 12/2001

(Continued)

OTHER PUBLICATIONS

Hanamori, Takamitsu. Chemical Stimulation of the Thalamic Reticular Nucleus Inhibits the Neuronal Activity of the Posterior Insular Cortex in Rats. Chemical Senses, vol. 28, No. 8, pp. 717-728. Oxford University Press, 2003.*

(Continued)

*Primary Examiner*—Kristen D. Mullen
*Assistant Examiner*—Eugene T Wu
(74) *Attorney, Agent, or Firm*—Christopher S. L. Crawford; Peter Lando; Melissa Acosta

(57) ABSTRACT

The present invention involves a method and a system for using electrical stimulation and/or chemical stimulation to treat depression. More particularly, the method comprises surgically implanting an electrical stimulation lead and/or catheter that is in communication with a predetermined site which is coupled to a signal generator and/or infusion pump that release either an electrical signal and/or a pharmaceutical resulting in stimulation of the predetermined site thereby treating the mood and/or anxiety disorder.

11 Claims, 10 Drawing Sheets

U.S. PATENT DOCUMENTS

| | | | |
|---|---|---|---|
| 5,342,410 A | 8/1994 | Braverman | |
| 5,423,877 A | 6/1995 | Mackey | |
| 5,458,631 A | 10/1995 | Xavier | |
| 5,470,846 A | 11/1995 | Sandyk et al. | |
| 5,540,734 A | 7/1996 | Zabara et al. | |
| 5,585,118 A | 12/1996 | Stoll | |
| 5,601,835 A | 2/1997 | Sabel et al. | |
| 5,683,422 A | 11/1997 | Rise | |
| 5,707,335 A | 1/1998 | Howard et al. | |
| 5,711,316 A | 1/1998 | Elsberry et al. | |
| 5,713,923 A | 2/1998 | Ward et al. | |
| 5,716,377 A | 2/1998 | Rise et al. | |
| 5,735,505 A | 4/1998 | Walton | |
| 5,735,814 A | 4/1998 | Elsberry et al. | |
| 5,750,103 A | 5/1998 | Cherksey | |
| 5,752,911 A | 5/1998 | Canedo et al. | |
| 5,779,694 A | 7/1998 | Howard et al. | |
| 5,792,186 A | 8/1998 | Rise | |
| 5,814,014 A | 9/1998 | Elsberry et al. | |
| 5,832,932 A | 11/1998 | Elsberry et al. | |
| 5,833,709 A | 11/1998 | Rise et al. | |
| 5,840,069 A | 11/1998 | Robinson | |
| 5,853,385 A | 12/1998 | Emerich et al. | |
| 5,873,849 A | 2/1999 | Bernard | |
| 5,921,245 A | 7/1999 | O'Donnell, Jr. | |
| 5,938,688 A | 8/1999 | Schiff | |
| 5,975,085 A | 11/1999 | Rise | |
| 5,978,702 A | 11/1999 | Ward et al. | |
| 6,015,786 A | 1/2000 | Mascarenhas et al. | |
| 6,016,449 A | 1/2000 | Fischell et al. | |
| 6,036,459 A | 3/2000 | Robinson | |
| 6,042,579 A | 3/2000 | Elsberry et al. | |
| 6,051,017 A | 4/2000 | Loeb et al. | |
| 6,093,180 A | 7/2000 | Elsberry | |
| 6,094,598 A | 7/2000 | Elsberry et al. | |
| 6,128,537 A * | 10/2000 | Rise | 607/45 |
| 6,129,685 A | 10/2000 | Howard, III | |
| 6,132,361 A | 10/2000 | Epstein et al. | |
| 6,161,045 A | 12/2000 | Fischell et al. | |
| 6,176,242 B1 | 1/2001 | Rise | |
| 6,216,030 B1 | 4/2001 | Howard et al. | |
| 6,227,203 B1 | 5/2001 | Rise et al. | |
| 6,230,049 B1 | 5/2001 | Fischell et al. | |
| 6,248,126 B1 | 6/2001 | Lesser et al. | |
| 6,251,115 B1 | 6/2001 | Williams et al. | |
| 6,251,669 B1 | 6/2001 | Luskin | |
| 6,263,237 B1 | 7/2001 | Rise | |
| 6,278,895 B1 | 8/2001 | Bernard | |
| 6,353,754 B1 | 3/2002 | Fischell et al. | |
| 6,353,762 B1 | 3/2002 | Baudino et al. | |
| 6,356,784 B1 * | 3/2002 | Lozano et al. | 607/2 |
| 6,366,813 B1 | 4/2002 | DiLorenzo | |
| 6,399,574 B1 | 6/2002 | McCabe et al. | |
| 6,418,344 B1 | 7/2002 | Rezai et al. | |
| 6,425,852 B1 | 7/2002 | Epstein et al. | |
| 6,463,328 B1 | 10/2002 | John | |
| 6,473,639 B1 | 10/2002 | Fischell et al. | |
| 6,514,937 B1 | 2/2003 | Mascarenhas | |
| 6,539,263 B1 | 3/2003 | Schiff et al. | |
| 6,567,696 B2 | 5/2003 | Voznesensky et al. | |
| 6,591,138 B1 | 7/2003 | Fischell et al. | |
| 6,592,509 B1 | 7/2003 | Hunter, Jr. | |
| 6,594,880 B2 | 7/2003 | Elsberry | |
| 6,597,954 B1 | 7/2003 | Pless et al. | |
| 6,609,030 B1 | 8/2003 | Rezai et al. | |
| 6,609,031 B1 | 8/2003 | Law et al. | |
| 6,620,151 B2 | 9/2003 | Blischak et al. | |
| 6,629,973 B1 | 10/2003 | Wardell et al. | |
| 6,666,845 B2 | 12/2003 | Hooper et al. | |
| 6,708,064 B2 | 3/2004 | Rezai | |
| 6,712,753 B2 | 3/2004 | Manne | |
| 6,735,474 B1 | 5/2004 | Loeb et al. | |
| 6,735,475 B1 | 5/2004 | Whitehurst et al. | |
| 6,782,292 B2 | 8/2004 | Whitehurst | |
| 6,819,956 B2 | 11/2004 | DiLorenzo | |
| 6,871,098 B2 | 3/2005 | Nuttin et al. | |
| 6,898,455 B2 | 5/2005 | Anderson et al. | |
| 6,907,280 B2 | 6/2005 | Becerra et al. | |
| 2002/0013612 A1 * | 1/2002 | Whitehurst | 607/45 |
| 2002/0058867 A1 | 5/2002 | Breiter et al. | |
| 2002/0062143 A1 * | 5/2002 | Baudino et al. | 607/116 |
| 2002/0091419 A1 | 7/2002 | Firlik et al. | |
| 2002/0151939 A1 * | 10/2002 | Rezai | 607/40 |
| 2002/0169485 A1 | 11/2002 | Pless et al. | |
| 2003/0028072 A1 | 2/2003 | Fischell et al. | |
| 2003/0032001 A1 | 2/2003 | Broderick | |
| 2003/0097159 A1 | 5/2003 | Schiff et al. | |
| 2003/0149457 A1 | 8/2003 | Tcheng et al. | |
| 2003/0181954 A1 | 9/2003 | Rezai | |
| 2004/0092010 A1 | 5/2004 | Altaba et al. | |
| 2005/0027284 A1 | 2/2005 | Lozano et al. | |
| 2005/0033379 A1 | 2/2005 | Lozano et al. | |
| 2005/0143799 A1 | 6/2005 | Black et al. | |
| 2005/0143800 A1 | 6/2005 | Lando et al. | |

FOREIGN PATENT DOCUMENTS

| | | |
|---|---|---|
| WO | WO-03043690 | 5/2003 |
| WO | WO-03063951 | 8/2003 |

OTHER PUBLICATIONS

Barbas et al, "Projections from the Amygdala to Basoventral and Mediodorsal Prefrontal Regions in the Rhesus Monkey," The Journal of Comparative Neurology vol. 300, 1990, pp. 549-571.

Barbas et al, "Topographically Specific Hippocampal Projections Target Functionally Distinct Prefrontal Areas in the Rhesus Monkey," Hippocampus vol. 5, 1995, pp. 511-533.

Bjorklund et al, "Cell Replacement therapies for Central Nervous System Disorders," Nature Neuroscience vol. 3, No. 6, Jun. 2000, pp. 537-544.

Bremmer, J.D., "Structural Changes in the Brain in Depression and relationship to Symptom Recurrence," CNS Spectrums, vol. 7, No. 2, Feb. 2002, pp. 129-139.

Caetano et al, "Anatomical MRI Study of Hippocampus and Amygdala in Patients with Current and Remitted Major Depression," Psychiatry Research: Neuroimaging vol. 132, 2004, pp. 141-147.

Capel et al, "The influence of electrostimulation on hexobarbital induced loss of righting reflex in rats," *Acupunct. Electrother. Res.* 7(1): 17-26, 1982.

Cosgrove et al, "Psychosurgery," Neurosurgery Clinicls of North America vol. 6 No. 1, Jan. 1995, pp. 167-176.

Delbello et al, "Magnetic Resonance Imaging Analysis of Amygdala and other Subcortical Brain Regions in Adolescents with Bipolar Disorders," Bipolar Disorders vol. 6, 2004, pp. 43-52.

Diamond et al, "Preclinical Research on Stress, Memory and the Brain in the Development of Pharmacotherapy for Depression," European Neuropsychopharmacology vol. 14, 2004 pp. S491-S495.

Dougherty et al., "Cerebral metabolic correlates as potential predictors of response to anterior cingulotomy for treatment of major depression," *J. Neurosurg.*, 99(6): 1010-7, 2003.

Drevets et al, "Functional Anatomical Correlates of Antidepressants Drug Treatment Assessed Using PET Measures of Regional Glucose Metabolism," European Neuropsychopharmacology vol. 12, 2002, pp. 527-544.

Drevets et al, "Subgenual Prefrontal Cortex Abnormalities in Mood Disorders," Nature vol. 386, Apr. 24, 1997, pp. 824-827.

Ebmeier et al, "Cerebral Perfusion Correlates of Depressed Mood," British Journal of Psychiatry vol. 178, 1997, pp. 77-81.

Fossati et al, "Neuroplasticity: from MRI to Depressive Symptoms," European Neuropsychopharmacology vol. 14, 2004, pp. S503-S510.

Galynker et al, "Hypofrontality and Negative Symptoms in Major Depressive Disorder," The Journal of Nuclear Medicine vol. 39, No. 4, Apr. 1998, pp. 608-612.
Goldapple et al, "Modulation of Cortical-Limbic Pathways in Major Depression," Arch Gen Psychiatry vol. 61, Jan. 2004, pp. 34-41.
Haberfer et al, "No Tissue Damage by Chronic Deep Brain Stimulation in Parkinson's Disease," Annals of Neurology vol. 48 No. 3, Sep. 2000, pp. 372-376.
Haldane et al, "New Insights Help Define the Pathophysiology of Bipolar Affective Disorder: Neuroimaging and Neuropathology Findings," Progress in Neuro-Psychopharmacology & Biological Psychiatry vol. 28, 2004, pp. 943-960.
Hilty et al, "A Review of Bipolar Disorder Among Adults," Psychiatric Services vol. 50, 1999, pp. 201-213.
Huerta et al, "Low-Frequency Stimulation at the Troughs of θ-Oscillation Induces Long-Term Depression of Previously Potentiated CA1 Synapses," Journal of Neurophysiology vol. 75, No. 2, Feb. 1996, pp. 877-884.
Jimenez et al., "A Patient with a Resistant Major Depression Disorder Treated with Deep Brain Stimulation in the Inferior Peduncle," *Neurosurgery*, 57(3): 585-593, 2005.
Keightley et al., "An fMRI study investigating cognitive modulation of brain regions associated with emotional processing of visual stimuli," *Neuropsychologia*, 41(5): 585-96, 2003.
Keightley et al., "Personality influences limbic-cortical interactions during sad mood induction," *Neuroimage*, 20(4): 2031-9, 2003.
Kennedy et al., "Changes in regional brain glucose metabolism measured with positron emission tomography after paroxetine treatment of major depression," *Am. J. Psychiatry*, 158(6): 899-905, 2001.
Lange et al, "Enlarged Amygdala Volume and Reduced Hippocampal Volume in Young Women with Major Depression," Psychological Medicine vol. 34, 2004, pp. 1059-1064.
Liotti et al, "Differential Limbic-Cortical Correlates of Sadness and Anxiety in Healthy Subjects: Implications for Affective Disorders," Soceity of Biological Psychiatry vol. 48, 2000, pp. 30-42.
Liotti et al., "The role of functional neuroimaging in the neuropsychology of depression," *J. Clin. Exp. Neuropsycol.*, 23(1): 121-36, 2001.
Liotti et al., "Unmasking disease-specific cerebral blood flow abnormalities: mood challenge in patients with remitted unipolar depression," *Am. J. Psychiatry*, 159(11): 1830-40, 2002.
Little et al, "How Common is Resistance to Treatment in Recurrent, Nonpsychotic Geriatic Depression?", American Journal of Psychiatry 155: Aug. 8, 1998, pp. 1035-1038.
Mayberg et al, "Reciprocal Limbic-Cortical Function and Negative Mood: Converging PET Findings in Depression and Normal Sadness," Am J. Psychiatry 156:May 5, 1999, pp. 675-682.
Mayberg et al, "Regional Metabolic Effects of Fluoxetine in Major Depression: Serial Changes and Relationship to Clinical Response," Biological Psychiatry vol. 48, 2000, pp. 830-843.
Mayberg et al., "Cingulate function in depression: a potential predictor of treatment response," *Neuroreport*, 8(4): 1057-61, 1997.
Mayberg et al., "Deep brain stimulation for treatment-resistant depression," *Neuron*, 45(5): 651-60, 2005.
Mayberg et al., "Depression in Parkinson's disease: a biochemical and organic viewpoint," *Adv. Neurol.*, 65: 49-60, 1995.
Mayberg et al., "Paralimbic frontal lobe hypometabolism in depression associated with Huntington's disease," *Neurology*, 42(9): 1791-7, 1992.
Mayberg et al., "Paralimbic hypoperfusion in unipolar depression," *J. Nucl. Med.*, 35(6): 929-34, 1994.
Mayberg et al., "Selective hypometabolism in the inferior frontal lobe in depressed patients with Parkinson's disease," *Ann. Neurol.*, 28(1): 57-64, 1990.
Mayberg et al., "The Functional Neuroanatomy of the Placebo Effect", American Journal of Psychiatry vol. 159, 2002, pp. 728-737.
Mayberg, "Clinical correlates of PET- and SPECT-identified defects in dementia," *J. Clin. Psychiatry*, 55 Suppl.: 12-21, 1994.
Mayberg, "Depression, II: localization of pathophysiology," *Am. J. Psychiatry*, 159(12): 1979, 2002.
Mayberg, "Frontal lobe dysfunction in secondary depression," *J. Neuropsychiatry Clin. Neurosci.*, 6(4): 428-42, 1994.
Mayberg, "Positron emission tomography imaging in depression: a neural systems perspective," *Neuroimaging Clin. N. Am.*, 13(4): 805-15, 2003.
Mayberg, Helen, "Modulating Dysfunctional Limbic-Cortical Cicuits in Depression: towards development of brain-based algorithms for diagnosis and optimised treatment," British Medical Bulletin vol. 65, 2003, pp. 193-207.
Mayberg, Helen, "Modulating Limbic-Cortical Circuits in Depression: Targets of Antidepressant Treatments," Seminars in Clinical Neuropsychiatry vol. 7, No. 4, Oct. 2002, pp. 255-268.
Mayberg, Helen: "Limbic-Cortical Dysregulation: A Proposed Model of Depression," Journal of Neuropsychiatry vol. 9 No. 3, 1997, pp. 471-481.
Patterson et al., "Electrostimulation: addiction treatment for the coming millenium," *J. Altern. Complement Med.*, 2(4): 485-91, 1996.
Patterson, "Effects of neuro-electric therapy (N.E.T.) in drug addiction: interim report," *Bull. Narc.*, 28(4): 55-62, 1976.
Patterson, "Electrostimulation and opiate withdrawal," *Br. J. Psychiatry*, 146: 213, 1985.
Patterson, "Electrotherapy: addictions and neuroelectric therapy," *Nurs. Times*, 75(48): 2080-3, 1979.
Patterson, "Neuro-electric therapy: criticisms of the 1984 Bethlem Study," *Br. J. Addict.*, 84(7): 818, 1989.
Phillips et al, "Neurobiology of Emotion Perseption I: The Neural Basis of Normal Emotion Perception," Biol Psychiatry vol. 54, 2003, pp. 504-514.
Phillips et al, "Neurobiology of Emotion Preception II: Implications for Major Psychiatric Disorders," Biol Psychiatry vol. 54, 2003, pp. 515-528.
Rauch, S. L., "Neuroimaging and Neurocircuitry Models Pertaining to the Neurosurgical Treatment of Psychiatric Disorders," Neurosurg Clin N Am vol. 14, 2003, pp. 213-223.
Sander et al, "The Human Amygdala: An Evolved System for Relevance Detection," Reviews in Neurosciences vol. 14, 2003, pp. 303-316.
Seminowicz et al, "Limbic-frontal Circuitry in Major Depression: A Path Modeling Metanalysis," Neuroimage vol. 22, 2004, pp. 409-418.
Sheline, Yvette, "3D MRI Studies of Neuroanatomic Changes in Unipolar Major Depression: The Role of Stress and Medical Comorbidity," Biol Psychiatry vol. 48, 2000, pp. 791-800.
Soares et al, "The Functional Neuroanatomy of Mood Disorders," J. Psychiat. Res. vol. 31 No. 4, 1997, pp. 393-432.
Starkstein et al., "Depression and cognitive impairment in Parkinson's disease," *Brain*, 112 (Pt. 5): 1141-53, 1989.
Stefurak et al., "Deep brain stimulation for Parkinson's disease dissociates mood and motor circuits: a functional MRI case study," *Mov. Disord.*, 18(12): 1508-16, 2003.
Temple, Sally, "Stem Cell Plasticity—Building the Brain of Our dreams," Nature Reviews/Neuroscience vol. 2, Jul. 2001, pp. 513-520.
Velasco et al., "Neurobiological Background for Performing Surgical Intervention in the Inferior Thalmic Peduncle for Treatment of Major Depression Disorders," *Neurosurgery*, 57(3): 439-448, 2005.
Videbech et al, "Hippocampal Volume and Depression: A Meta-Analysis of MRI Studies," Am. J. Psychiatry vol. 161, No. 11, Nov. 2004, pp. 1957-1966.
Weissman et al, "Cross-National Epidemiology of Major Depression and Bipolar Disorder," JAMA vol. 276, No. 4, Jul. 24/31, 1996, pp. 293-299.
Andy et al, "Thalamic Stimulation Effects on Reactive Depression", App Neurophysiol. 50: 324-329 (1987).

* cited by examiner

A

B

METHOD OF TREATING MOOD DISORDERS AND/OR ANXIETY DISORDERS BY BRAIN STIMULATION

CROSS-REFERENCE TO RELATED APPLICATIONS

The present application claims priority to U.S. Provisional Application No. 60/567,332 filed Apr. 30, 2004, which is incorporated herein by reference in its entirety.

TECHNICAL FIELD

This invention relates to neuronal tissue stimulation for treating anxiety disorders and/or mood disorders, and more particularly to modulating neuronal tissue at a predetermined stimulation site in brain tissue.

BACKGROUND OF THE INVENTION

Recent estimates indicate that more than 19 million Americans over the age of 18 years experience a depressive illness each year. The American Psychiatric Association recognizes several types of clinical depression, including Mild Depression (Dysthymia), Major Depression, and Bipolar Disorder (Manic-Depression). Major Depression is defined by a constellation of chronic symptoms that include sleep problems, appetite problems, anhedonia or lack of energy, feelings of worthlessness or hopelessness, difficulty concentrating, and suicidal thoughts. Approximately 9.2 million Americans suffer from Major Depression, and approximately 15 percent of all people who suffer from Major Depression take their own lives. Bipolar Disorder involves major depressive episodes alternating with high-energy periods of rash behavior, poor judgment, and grand delusions. An estimated one percent of the American population experiences Bipolar Disorder annually.

Significant advances in the treatment of depression have been made in the past decade. Since the introduction of selective serotonin reuptake inhibitors (SSRIs), e.g., Prozac®, many patients have been effectively treated with anti-depressant medication. New medications to treat depression are introduced almost every year, and research in this area is ongoing. However, an estimated 10 to 30 percent of depressed patients taking an anti-depressant are partially or totally resistant to the treatment. Those who suffer from treatment-resistant depression have almost no alternatives. Thus, there is a need to develop alternative treatments for these patients.

The use of electrical stimulation for treating neurological disease, including such disorders as movement disorders including Parkinson's disease, essential tremor, dystonia, and chronic pain, has been widely discussed in the literature. It has been recognized that electrical stimulation holds significant advantages over lesioning since lesioning destroys the nervous system tissue. In many instances, the preferred effect is to modulate neuronal activity. Electrical stimulation permits such modulation of the target neural structures and, equally importantly, does not require the destruction of nervous tissue. Such electrical stimulation procedures include electroconvulsive therapy (ECT), repetitive transcranial (rTMS) magnetic stimulation and vagal nerve stimulation (VNS).

Efforts have been made to treat psychiatric disorders with peripheral/cranial nerve stimulation. Recently, partial benefits with vagus nerve stimulation in patients with depression have been described in U.S. Pat. No. 5,299,569. Another example of electrical stimulation to treat depression is described in U.S. Pat. No. 5,470,846, which discloses the use of transcranial pulsed magnetic fields to treat depression. Yet further, U.S. Pat. No. 5,263,480 describes that stimulation of the vagus nerve may control depression and compulsive eating disorders and U.S. Pat. No. 5,540,734 teaches stimulation of the trigeminal or glossopharyngeal nerves for psychiatric illness, such as depression.

Deep brain stimulation (DBS) has been applied to the treatment of central pain syndromes and movement disorders, and it is currently being explored as a therapy for epilepsy. For instance, U.S. Pat. No. 6,016,449 and U.S. Pat. No. 6,176,242 disclose a system for the electrical stimulation of areas in the brain for the treatment of certain neurological diseases such as epilepsy, migraine headaches and Parkinson's disease.

Various electrical stimulation and/or drug infusion devices have been proposed for treating neurological disorders. Some devices stimulate through the skin, such as electrodes placed on the scalp. Other devices require significant surgical procedures for placement of electrodes, catheters, leads, and/or processing units. These devices may also require an external apparatus that needs to be strapped or otherwise affixed to the skin.

However, despite the aforesaid available treatments, there are patients with mood and/or anxiety disorders that remain treatment refractory and chronically disabled. For these severely ill and disabled patients, novel therapies are required.

BRIEF SUMMARY OF THE INVENTION

The present invention relates to stimulation techniques (e.g., electrical and/or chemical and/or magnetic) not considered in the prior art to play a role in affective disorders. In certain embodiments, the invention uses electrical stimulation and/or chemical stimulation (i.e., one or more pharmaceuticals) to treat affective disorders, such as mood and/or anxiety disorders. According to one embodiment of the invention, the stimulation modulates areas of the brain that exhibit altered activity in patients relative to psychiatrically normal control subjects, thereby treating or preventing affective disorders, for example depression and/or anxiety disorders. Such stimulation is likely to be produced by electrical stimulation, an excitatory neurotransmitter agonist(s) (e.g., norepinephrine), an inhibitory neurotransmitter antagonist(s), and/or a medication that increases the level of an excitatory neurotransmitter (e.g., flouxetine (Prozac®), trazodone).

In addition to electrical and chemical stimulation, other types of stimulations can also be used, for example, magnetic, thermal and/or ultrasonic stimulation can be used to modulate the gray matter and white matter tracts in a predetermined area. Magnetic stimulation can be provided by internally implanted probes or by externally applied directed magnetic fields. Thermal stimulation can be provided by using implanted probes that are regulated to produce or emit heat and/or cold temperatures.

Alternatively, affective disorders can be treated by utilizing other known methods to alter the neuronal activity of the above mentioned predetermined sites. For example, lesioning and mechanical disruption can be used as described by U.S. Pat. Nos. 6,629,973, and 3,653,385.

Certain embodiments of the present invention involve a method and a therapeutic system having a surgically implanted device in communication with a predetermined site. The device or stimulation system is operated to stimulate the predetermined site thereby treating the mood and/or anxiety disorder. The device can include a stimulation portion or a probe, for example, an electrode, an electrode assembly (e.g., electrical stimulation lead), pharmaceutical-delivery assembly (e.g., catheters) or combinations of these and/or a signal generator or signal source or pulse generating source (i.e. (i.e., electrical signal source, chemical signal source (i.e., pharmaceutical delivery pump) or magnetic signal source). The probe may be coupled to the signal source, pharmaceutical delivery pump, or both which, in turn, is operated to stimulate the predetermined treatment site. Yet further, the probe and the signal generator or source can be incorporated together, wherein the signal generator and probe are formed into a unitary or single unit, such unit may comprise, one, two or more electrodes. These devices are known in the art as microstimulators, for example, Bion™ which is manufactured by Advanced Bionics Corporation.

In certain embodiments, the present invention comprises a method of treating the mood and/or anxiety disorder comprising the steps of: surgically implanting a stimulation portion or an electrode, wherein after implantation the stimulation portion or electrode is in communication with a predetermined site; coupling the stimulation portion or electrode to a signal source or pulse generating source; and generating a signal to modulate the predetermined site thereby treating the mood and/or anxiety disorder.

Another embodiment of the present invention comprises a method of treating the mood and/or anxiety disorder comprising the steps of: surgically implanting an electrical stimulation lead having a proximal end and a stimulation portion, wherein after implantation the stimulation portion is in communication with a predetermined site; coupling the proximal end of the lead to a signal generator; and generating an electrical signal with the signal generator to modulate the predetermined site thereby treating the mood and/or anxiety disorder. The mood disorder is selected from the group consisting of major depressive disorder, bipolar disorder, and dysthymic disorder. The anxiety disorder is selected from the group consisting of panic disorder, post-traumatic stress disorder, obsessive-compulsive disorder and phobic disorder.

In further embodiments, the method can comprise the steps of: surgically implanting a catheter having a proximal end coupled to a pump and a discharge portion for infusing a dosage of a pharmaceutical, wherein after implantation the discharge portion of the catheter is in communication with the predetermined stimulation site; and operating the pump to discharge the pharmaceutical through the discharge portion of the catheter into the stimulation site thereby treating the mood and/or anxiety disorder. The pharmaceutical is selected from the group consisting of inhibitory neurotransmitter agonist, an excitatory neurotransmitter antagonist, an agent that increases the level of an inhibitory neurotransmitter, an agent that decrease the level of an excitatory neurotransmitter, and a local anesthetic agent. It is envisioned that chemical stimulation or pharmaceutical infusion can be preformed independently of electrical stimulation and/or in combination with electrical stimulation.

It is envisioned that the predetermined site can be the hypothalamus. Thus, any site that is in communication with the hypothalamus is within the scope of the present invention. Other sites can also be stimulated, for example, but not limited to the inferior thalamic peduncles (IPT) and/or the thalamic reticular nuclei.

Stimulation of the hypothalamus and/or myelinated and/or non-myelinated pathways that are associated with the hypothalamus can result in an alleviation or modulation of the mood and/or anxiety disorder. Modulating the hypothalamus via electrical and/or chemical stimulation (i.e., pharmaceutical) can result in increasing, decreasing, masking, altering, overriding or restoring neuronal activity resulting in treatment of the mood and/or anxiety disorder. Thus, stimulation of the above mentioned predetermined areas includes stimulation of the gray matter and white matter tracts associated therewith that results in an alleviation or modulation of the mood and/or anxiety disorder. Associated white matter tracts includes the surrounding or adjacent white matter tracts leading to or from or white matter tracts that are contiguous with the area.

In further embodiments, stimulation of the inferior thalamic peduncle the surrounding or adjacent white matter tracts leading to or from the inferior thalamic peduncle or white matter tracts that are contiguous with the inferior thalamic peduncle results in an alleviation or modulation of the mood and/or anxiety disorder. Modulating the inferior thalamic peduncle via electrical and/or chemical stimulation (i.e., pharmaceutical) can result in increasing, decreasing, masking, altering, overriding or restoring neuronal activity resulting in treatment of the mood and/or anxiety disorder.

Yet further, stimulation of thalamic reticular nucleus and/or myelinated and/or non-myelinated pathways that are associated with the thalamic reticular nucleus can result in an alleviation or modulation of the mood and/or anxiety disorder. Modulating the thalamic reticular nucleus via electrical and/or chemical stimulation (i.e., pharmaceutical) can result in increasing, decreasing, masking, altering, overriding or restoring neuronal activity resulting in treatment of the mood and/or anxiety disorder.

Another embodiment of the present invention is a method of treating a mood and/or anxiety disorder comprising the steps of: surgically implanting an electrical stimulation lead having a proximal end and a stimulation portion, wherein after implantation the stimulation portion is in communication with a first predetermined site selected from the group consisting of hypothalamus, inferior thalamic peduncle and thalamic reticular nucleus; surgically implanting a catheter having a proximal end coupled to a pump and a discharge portion for infusing a dosage of a pharmaceutical, wherein after implantation the discharge portion of the catheter is in communication with a second predetermined stimulation site selected from the group consisting of hypothalamus, inferior thalamic peduncle and thalamic reticular nucleus; and coupling the proximal end of the lead to a signal generator; generating an electrical signal with the signal generator to modulate the predetermined site; and operating the pump to discharge the pharmaceutical through the discharge portion of the catheter into the predetermined site thereby treating the mood and/or anxiety disorder.

Other embodiments of the present invention include a system for treating subjects with mood and/or anxiety disorders. The therapeutic system comprises an electrical stimulation lead that is implanted into the subject's brain, the lead comprises at least one electrode that is in communication with the hypothalamus, inferior thalamic peduncle, or thalamic reticular nucleus and delivers electrical signals to hypothalamus, inferior thalamic peduncle, or thalamic reticular nucleus in response to received signals; and a signal generator that generates signals for transmission to the electrodes of the lead resulting in delivery of electrical signals to the predetermined site thereby treating the mood and/or anxiety disorder. The electrical stimulation lead may comprise one electrode or a plurality of electrodes in or around the target area. Still further, the signal generator is implanted in the subject's body.

Another example of a therapeutic system is a catheter having a proximal end coupled to a pump and a discharge portion for infusing a dosage of a pharmaceutical, wherein after implantation the discharge portion of the catheter is in communication with a predetermined stimulation site; and a pump to discharge the pharmaceutical through the discharge portion of the catheter into the predetermined stimulation site thereby treating the mood and/or anxiety disorder.

In a specific embodiment, the catheter of the therapeutic system can be a combination catheter and lead. Thus, the system also comprises a signal generator that generates signals for transmission to the electrodes of the lead resulting in delivery of electrical signals to the predetermined site thereby treating the mood and/or anxiety disorder.

Still further, another therapeutic system comprises a device that is surgically implanted into the subject such that the device is in communication with a predetermined site. An exemplary device includes a microstimulator (i.e., Bion™ manufactured by Advanced Bionics Corporation) in which the device contains a generating portion and at least one electrode in a single unit. In further embodiments, a lead assembly is associated with at least one electrode of the microstimulator such that the lead can stimulate the predetermined site not in direct contact with the microstimulator.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings.

FIG. 4A shows axial and frontal MRI sections showing the 8 contact electrodes' placement in both sides. FIG. 4B shows the area within the squares is analyzed anatomically on the horizontal (Hv −0.5) and frontal sections (Fa 7.5) of the Schaltenbrand and Wahren atlas. Abbreviations: Cma=anterior commisure, Fx=fornix, Hpth=hypothalamus, Put=putamen, Pl=lateral pallidus, Pm=medial pallidus, Cpip=posterior branch internal capsule, Zi=zona incerta, Tmth=mammillo-thalamic tract, Raprl=Prelemniscal radiations, Pu=pulvinar, Cd=caudate nucleus, Cpig=genu of internal capsule, Pd th if=inferior thalamic peduncle (ITP in this paper), Rtpo=nucleus reticularis polaris, Vm=nucleus ventralis hipothalami, An Pd=ansa lenticularis, B=Meynert's basal nucleus and II=optic tract, R=right electrode, L=left electrode (28).

FIGS. 6A and 6B (left side) show surface negative recruiting—like responses produced by 6/sec unilateral supra-threshold stimulation of Rtpo and ITP predominant at the bilateral fronto-polar regions. FIGS. 6A and 6B (right side) show surface negative DC shifts and desynchronization produced by 60/sec unilateral supra-threshold stimulation of Rtpo and ITP with similar distribution to that of the recruiting responses.

FIG. 7A shows ZDS. FIG. 7B shows: HAM-D and BDI. The arrows indicate electrode insertion. Double blind trial is indicated by the bar in the bottom of the figure. The horizontal line indicates the limit of normal values.

FIG. 8A shows the results for Wisconsin Card Sorting Test. FIG. 8B shows the results for Finger Tapping Test. FIGS. 8C-8D shows the results for auditory verbal learning (Rey Test, FIG. 8C) and Corsi Block Tapping Test (nonverbal memory, FIG. 8D). The horizontal lines indicate limit of normal values. The bar in the bottom of the graphics indicates double blind trial. Arrows show the effect of electrodes insertion.

FIG. 9A shows during the 2 years prior to surgery, scores were high with brief remissions coinciding with different antidepressive treatments that included the following: 1) Ten sessions of electroconvulsive therapy; 2) Change of medication to Bupropion 300 mg/day plus Lithium 900 mg/day; 3) Change of medication to Reboxetine 16 mg/day and Amitryptiline 50 mg/day, and 4) withdrawal of antidepressive drugs was accompanied by increase in HAM-D score of only 9 points. FIG. 9B shows post-operative evaluation is displayed, 5) Initial dramatic drop of HAM-D score which coincided with insertion of the stimulation-recording electrodes, 6) 1 week after (1 w) and prior to onset of electrical stimulation, HAM-D score rose to abnormal levels, 7) New decrease in HAM-D scores was coincident with deep brain stimulation, which reached normal values at 1 month and remained so during the period of ON stimulation (clear bar at bottom), and 8) 3 months after stimulation was turned OFF, scores showed spontaneous fluctuations that to date have not required re-medication or electrical stimulation (filled bar at bottom).

DETAILED DESCRIPTION OF THE INVENTION

Figure 1:
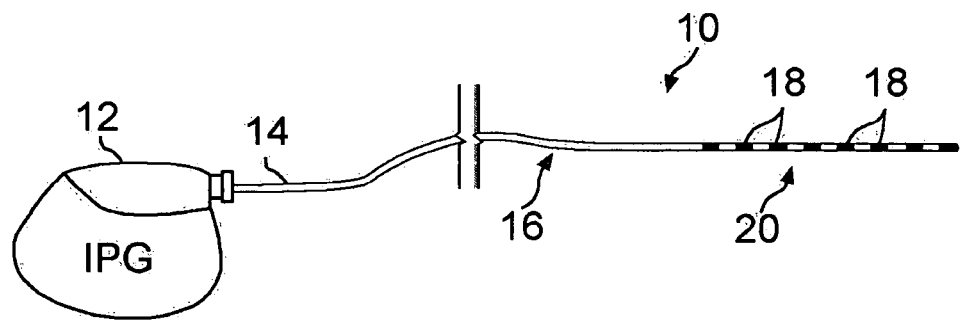
FIGS. 1A and 1B illustrate example electrical stimulation systems.
Figure 1:
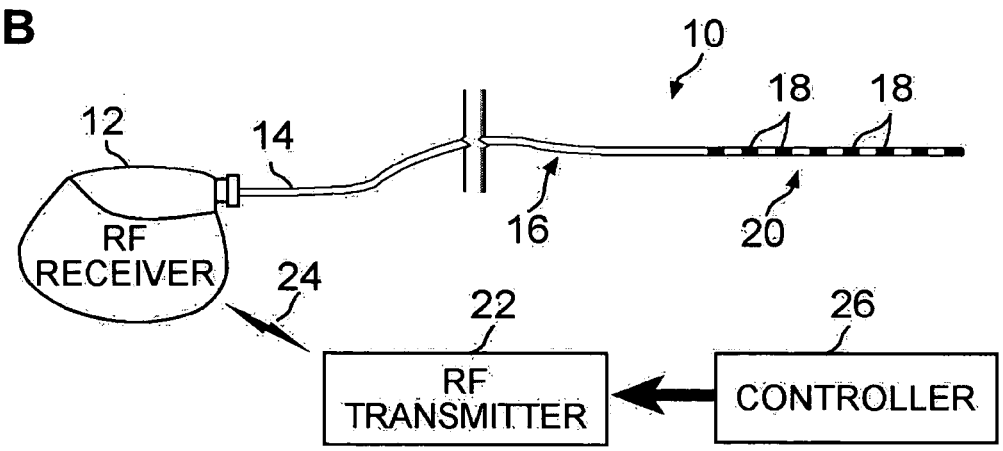
Figure 2:
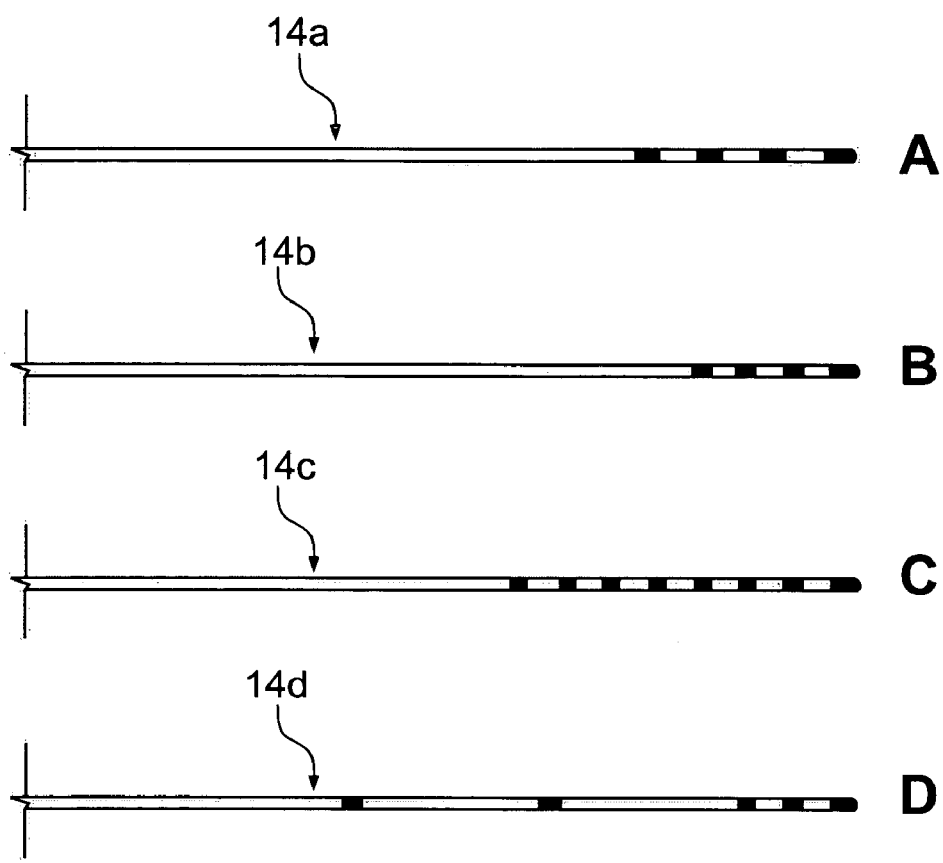
FIGS. 2A-2D illustrate example electrical stimulation leads that may be used in the present invention.

It is readily apparent to one skilled in the art that various embodiments and modifications can be made to the invention disclosed in this Application without departing from the scope and spirit of the invention.

I. DEFINITIONS

As used herein, the use of the word "a" or "an" when used in conjunction with the term "comprising" in the claims and/or the specification may mean "one," but it is also consistent with the meaning of "one or more," "at least one," and "one or more than one." Still further, the terms "having", "including", "containing" and "comprising" are interchangeable and one of skill in the art is cognizant that these terms are open ended terms.

As used herein the term "affective disorders" refers to a group of disorders that are commonly associated with co-morbidity of depression and anxiety symptoms.

As used herein the term "anxiety" refers to an uncomfortable and unjustified sense of apprehension that may be diffuse and unfocused and is often accompanied by physiological symptoms.

As used herein the term "anxiety disorder" refers to or connotes significant distress and dysfunction due to feelings of apprehension, guilt, fear, etc. Anxiety disorders include, but are not limited to panic disorders, posttraumatic stress disorder, obsessive-compulsive disorder and phobic disorders.

As used herein the term "depression" refers to a morbid sadness, dejection, or melancholy.

As used herein, the term "hypothalamus" refers to the defined area of hypothalamus as known by one of skill in the art, as well as the myelinated and/or non-myelinated pathways leading to and from the hypothalamus and myelinated and/or non-myelinated pathways that are associated, surround, adjacent and/or are contiguous with the hypothalamus.

As used herein, the term "inferior thalamic peduncle" or "ITP" refers to the defined area of inferior thalamic peduncle as known by one of skill in the art, as well as the surrounding or adjacent white matter tracts leading to and from inferior thalamic peduncle and/or white matter tracts that are contiguous with inferior thalamic peduncle. The surrounding or adjacent white matter tracts can include white matter tracts up to approximately 1 cm from the inferior thalamic peduncle.

As used herein, the term "in communication" refers to the stimulation lead and/or catheter being adjacent, in the general vicinity, in close proximity, or directly next to or directly on the predetermined stimulation site. Thus, one of skill in the art understands that the lead and/or catheter is "in communication" with the predetermined site of the brain if the stimulation results in a modulation of neuronal activity. Still further, "in communication" with brain tissue encompasses surrounding or adjacent myelinated and/or non-myelinated tissue or fibers leading to and from the brain tissue and/or myelinated and/or non-myelinated tissue or fibers that are contiguous with the brain tissue.

As used herein the term "limbic system" encompasses the amygdala, hippocampus, septum, cingulate gyrus, cingulate cortex, hypothalamus, epithalamus, anterior thalamus, mammillary bodies, and fornix. The limbic system has connections throughout the brain, more particularly with the primary sensory cortices, including the rhinencephalon for smell, the autonomic nervous system via the hypothalamus, and memory areas. Alterations in mood, emotion, and thought.

As used herein the term "mania" or "manic" refers to a disordered mental state of extreme excitement.

As used herein the term "mood" refers to an internal emotional state of a person.

As used herein the term "mood disorder" is typically characterized by pervasive, prolonged, and disabling exaggerations of mood and affect that are associated with behavioral, physiologic, cognitive, neurochemical and psychomotor dysfunctions. The major mood disorders include, but are not limited to major depressive disorder (also known as unipolar disorder), bipolar disorder (also known as manic depressive illness or bipolar depression), dysthymic disorder. Other mood disorders may include, but are not limited to major depressive disorder, psychotic; major depressive disorder, melancholic; major depressive disorder, seasonal pattern; postpartum depression; brief recurrent depression; late luteal phase dysphoric disorder (premenstrual dysphoria); and cyclothymic disorder.

As used herein the term "modulate" refers to the ability to regulate positively or negatively neuronal activity. Thus, the term modulate can be used to refer to an increase, decrease, masking, altering, overriding or restoring neuronal activity. Modulation of neuronal activity affects psychological and/or psychiatric activity of a subject.

As used herein, the term "neuronal" refers to a neuron which is a morphologic and functional unit of the brain, spinal column, and peripheral nerves.

As used herein, the term "obsessive-compulsive disorder" refers to an anxiety disorder in which an individual has developed rituals and/or compulsions that are performed to ward off an unwanted occurrence or to fulfill an obsession. One of the characteristics of this disorder is recurrent obsessions, i.e., persistent, intrusive thoughts and/or urges that are troublesome to the subject. Compulsions can be defined as repetitive behaviors performed in response to an obsession.

As used herein, the term "pharmaceutical" refers to a chemical or agent that is used as a drug. Thus, the term pharmaceutical and drug are interchangeable.

As used herein, the term "stimulate" or "stimulation" refers to electrical and/or chemical modulation of predetermined sites in the brain.

As used herein, the term "thalamic reticular nucleus" refers to the defined area of thalamic reticular nucleus as known by one of skill in the art, as well as the myelinated and/or non-myelinated pathways leading to and from the thalamic reticular nucleus and myelinated and/or non-myelinated pathways that are associated, surround, adjacent and/or are contiguous with the thalamic reticular nucleus.

As used herein, the term "treating" and "treatment" refers to modulating certain areas of the brain so that the subject has an improvement in the disease, for example, beneficial or desired clinical results. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. One of skill in the art realizes that a treatment may improve the disease condition, but may not be a complete cure for the disease.

II. ELECTRICAL STIMULATION DEVICES

FIGS. 1A and 1B illustrate example electrical stimulation systems 10 used to provide deep brain stimulation. Stimulation system 10 generates and applies a stimulus to a target area of the brain or is in communication with the target area of the brain, for example, a target area of the hypothalamus and/or the inferior thalamic peduncle (ITP), and/or the thalamic reticular nucleus. For the purposes of this application, the hypothalamus includes all the gray matter nuclei that are associated with the hypothalamus, as well as the any myelinated and/or non-myelinated pathways (i.e., afferent and/or efferent) associated with or is contiguous with the hypothalamus. Yet further, for the purposes of this application, ITP includes the defined area and/or fibers of the ITP, as well as the surrounding or adjacent white matter tracts leading to and from ITP and/or white matter tracts that are contiguous with ITP. Still further, for the purposes of this application, the thalamic reticular nucleus includes all the gray matter nuclei that are associated with the thalamic reticular nucleus, as well as any myelinated and/or non-myelinated pathways (i.e., afferent and/or efferent) associated with or contiguous with the thalamic reticular nucleus.

In general terms, stimulation system 10 includes an implantable pulse generating source, such as an electrical stimulation source 12 and an implantable stimulation portion, for example an electrode. In certain embodiments the electrode is comprised within an electrical stimulation lead 14. In operation, both of these primary components are implanted in the person's body. Stimulation source 12 is coupled to a connecting portion 16 of electrical stimulation lead 14. Stimulation source 12 controls the electrical signals transmitted to electrodes 18 located on a stimulating portion 20 of electrical stimulation lead 14, located adjacent the target brain tissue, according to suitable signal parameters (e.g., duration, intensity, frequency, etc.). A doctor, the patient, or another user of stimulation source 12 may directly or indirectly input signal parameters for controlling the nature of the electrical stimulation provided.

Another exemplary stimulation system or device includes a microstimulator (i.e., Bion™, manufactured by Advanced Bionics Corporation) in which the device contains a signal generating portion and at least one electrode in a the same unit or single unit, as defined in U.S. Pat. Nos. 6,051,017; 6,735,475; 6,735,474 and 6,782,292. In further embodiments, a lead assembly is associated with at least one electrode of the microstimulator such that the lead can stimulate the predetermined site not in contact with the microstimulator.

In one embodiment, as shown in FIG. 1A, stimulation source 12 includes an implantable pulse generator (IPG). One of skill in the art is aware that any commercially available implantable pulse generator can be used in the present invention, as well as a modified version of any commercially available pulse generator. Thus, one of skill in the are would be able to modify an IPG to achieve the desired results. An exemplary IPG is one that is manufactured by Advanced Neuromodulation Systems, Inc., such as the Genesis® System, part numbers 3604, 3608, 3609, and 3644. Another example of an IPG is shown in FIG. 1B, which shows stimulation source 12 including an implantable wireless receiver. An example of a wireless receiver may be one manufactured by Advanced Neuromodulation Systems, Inc., such as the Renew® System, part numbers 3408 and 3416. The wireless receiver is capable of receiving wireless signals from a wireless transmitter 22 located external to the person's body. The wireless signals are represented in FIG. 1B by wireless link symbol 24. A doctor, the patient, or another user of stimulation source 12 may use a controller 26 located external to the person's body to provide control signals for operation of stimulation source 12. Controller 26 provides the control signals to wireless transmitter 22, wireless transmitter 22 transmits the control signals and power to the wireless receiver of stimulation source 12, and stimulation source 12 uses the control signals to vary the signal parameters of electrical signals transmitted through electrical stimulation lead 14 to the stimulation site. An example wireless transmitter 122 may be one manufactured by Advanced Neuromodulation Systems, Inc., such as the Renew® System, part numbers 3508 and 3516.

FIGS. 2A-2D illustrate example electrical stimulation leads 14 that may be used to provide electrical stimulation to an area of the brain. As described above, each of the one or more leads 14 incorporated in stimulation system 10 includes one or more electrodes 18 adapted to be positioned near the target brain tissue and used to deliver electrical stimulation energy to the target brain tissue in response to electrical signals received from stimulation source 12. A percutaneous lead 14, such as example leads shown in FIGS. 2A-2D, includes one or more circumferential electrodes 18 spaced apart from one another along the length of lead 14. Circumferential electrodes 18 emit electrical stimulation energy generally radially in all directions.

III. IMPLANTATION OF ELECTRICAL STIMULATION DEVICES

In certain embodiments, for example, patients who are to have an electrical stimulation lead or electrode implanted into the brain, generally, first have a stereotactic head frame, such as the Leksell, CRW, or Compass, mounted to the patient's skull by fixed screws. However, frameless techniques may also be used. Subsequent to the mounting of the frame, the patient typically undergoes a series of magnetic resonance imaging sessions, during which a series of two dimensional slice images of the patient's brain are built up into a quasi-three dimensional map in virtual space. This map is then correlated to the three dimensional stereotactic frame of reference in the real surgical field. In order to align these two coordinate frames, both the instruments and the patient must be situated in correspondence to the virtual map. The current way to do this is to rigidly mount the head frame to the surgical table. Subsequently, a series of reference points are established to relative aspects of the frame and patient's skull, so that either a person or a computer software system can adjust and calculate the correlation between the real world of the patient's head and the virtual space model of the patient MRI scans. The surgeon is able to target any region within the stereotactic space of the brain with precision (e.g., within 1 mm). Initial anatomical target localization is achieved either directly using the MRI images, or indirectly using interactive anatomical atlas programs that map the atlas image onto the stereotactic image of the brain. As is described in greater detail elsewhere in this application, the anatomical targets may be stimulated directly or affected through stimulation in another region of the brain.

Based upon the coordinates, the electrical stimulation lead 14 can be positioned in the brain. Typically, an insertion cannula for electrical stimulation lead 14 is inserted through the burr hole into the brain, but a cannula is not required. For example, a hollow needle may provide the cannula. The cannula and electrical stimulation lead 14 may be inserted together or lead 14 may be inserted through the cannula after the cannula has been inserted.

Once electrical stimulation lead 14 has been positioned in the brain, lead 14 is uncoupled from any stereotactic equipment present, and the cannula and stereotactic equipment are removed. Where stereotactic equipment is used, the cannula may be removed before, during, or after removal of the stereotactic equipment. Connecting portion 16 of electrical stimulation lead 14 is laid substantially flat along the skull. Where appropriate, any burr hole cover seated in the burr hole may be used to secure electrical stimulation lead 14 in position and possibly to help prevent leakage from the burr hole and entry of contaminants into the burr hole. Example burr hole covers that may be appropriate in certain embodiments are illustrated and described in co-pending U.S. Application Nos. 60/528,604 and 60/528,689, both filed Dec. 11, 2003 and entitled "Electrical Stimulation System and Associated Apparatus for Securing an Electrical Stimulation Lead in Position in a Person's Brain", both of which are incorporated herein in their entirety.

Once electrical stimulation lead 14 has been inserted and secured, connecting portion 16 of lead 14 extends from the lead insertion site to the implant site at which stimulation source 12 is implanted. The implant site is typically a subcutaneous pocket formed to receive and house stimulation source 12. The implant site is usually positioned a distance away from the insertion site, such as near the chest, below the clavicle or alternatively near the buttocks or another place in the torso area. Once all appropriate components of stimulation system 10 are implanted, these components may be subject to mechanical forces and movement in response to movement of the person's body. A doctor, the patient, or another user of stimulation source 12 may directly or indirectly input signal parameters for controlling the nature of the electrical stimulation provided.

Although example steps are illustrated and described, the present invention contemplates two or more steps taking place substantially simultaneously or in a different order. In addition, the present invention contemplates using methods with additional steps, fewer steps, or different steps, so long as the steps remain appropriate for implanting an example stimulation system 10 into a person for electrical stimulation of the person's brain.

IV. INFUSION PUMPS

In further embodiments, it may be desirable to use a drug delivery system independent of or in combination with the DBS. Drug delivery may be used independent of or in combination with a lead/electrode to provide electrical stimulation and chemical stimulation. When used, the drug delivery catheter is implanted such that the proximal end of the catheter is coupled to a pump and a discharge portion for infusing a dosage of a pharmaceutical or drug. Implantation of the catheter can be achieved by combining data from a number of sources including CT, MRI or conventional and/or magnetic resonance angiography into the stereotactic targeting model. Thus, implantation of the catheter can be achieved using similar techniques as discussed above for implantation of electrical leads, which is incorporated herein. The distal portion of the catheter can have multiple orifices to maximize delivery of the pharmaceutical while minimizing mechanical occlusion. The proximal portion of the catheter can be connected directly to a pump or via a metal, plastic, or other hollow connector, to an extending catheter.

Any type of infusion pump can be used in the present invention. For example, "active pumping" devices or so-called peristaltic pumps are described in U.S. Pat. Nos. 4,692,147, 5,840,069, and 6,036,459. Peristaltic pumps are used to provide a metered amount of a drug in response to an electronic pulse generated by control circuitry associated within the device. An example of a commercially available peristaltic pump is SynchroMed® implantable pump from Medtronic, Inc., Minneapolis, Minn.

Other pumps that may be used in the present invention include accumulator-type pumps, for example certain external infusion pumps from Minimed, Inc., Northridge, Calif. and Infusaid® implantable pump from Strato/Infusaid, Inc., Norwood, Mass. Passive pumping mechanisms can be used to release an agent in a constant flow or intermittently or in a bolus release. Passive type pumps include, for example, but are not limited to gas-driven pumps described in U.S. Pat. Nos. 3,731,681 and 3,951,147; and drive-spring diaphragm pumps described in U.S. Pat. Nos. 4,772,263, 6,666, 845, 6,620,151. Pumps of this type are commercially available, for example, Model 3000® from Arrow International, Reading, Pa. and IsoMed® from Medtronic, Inc., Minneapolis, Minn.; AccuRx® pump from Advanced Neuromodulation Systems, Inc., Plano, Tex.

In certain embodiments, the catheter can be in the form of a lead catheter combination, similar to the ones described in U.S. Pat. No. 6,176,242 and U.S. Pat. No. 5,423,877.

V. IDENTIFYING A SUBJECT WITH AN AFFECTIVE DISORDER

Subjects to be treated using the present invention can be selected, identified and/or diagnosed based upon the accumulation of physical, chemical, and historical behavioral data on each patient. One of skill in the art is able to perform the appropriate examinations to accumulate such data. One type of examination can include neurological examinations, which can include mental status evaluations, which can further include a psychiatric assessment. Other types of examinations can include, but are not limited to, motor examination, cranial nerve examination, and neuropsychological tests (i.e., Minnesota Multiphasic Personality Inventory, Beck Depression Inventory, Y-BOCS, or Hamilton Rating Scale for Depression).

In addition to the above examinations, imaging techniques can be used to determine normal and abnormal brain function that can result in disorders. Functional brain imaging allows for localization of specific normal and abnormal functioning of the nervous system. This includes electrical methods such as electroencephalography (EEG), magnetoencephalography (MEG), single photon emission computed tomography (SPECT), as well as metabolic and blood flow studies such as functional magnetic resonance imaging (fMRI), and positron emission tomography (PET) which can be utilized to localize brain function and dysfunction.

VI. TREATMENT OF AN AFFECTIVE DISORDER

Initially there is an impetus to treat psychiatric disorders with direct modulation of activity in that portion of the brain causing the pathological behavior. In this regard there have been a large number of anatomical studies that have helped to identify the neural structures and their precise connections which are implicated in psychiatric activity/disorders. These are the structures that are functioning abnormally and manifesting in psychiatric/behavioral/addiction disorders. Numerous anatomical studies from autopsies, animal studies, and imaging such as computerized tomography (CT) scans, and magnetic resonance imaging (MRI) scans have demonstrated the role of these structures and their connections in psychiatric activity/disorders. In addition to these anatomical studies, a number of physiological techniques and diagnostic tools are used to determine the physiological aberrations underlying these disorders. This includes electrical methods such as electroencephalography (EEG), magnetoencephalography (MEG), as well as metabolic and blood flow studies such as functional magnetic resonance imaging (fMRI), and positron emission tomography (PET). The combination of the anatomical and physiological studies have provided increased insight into our understanding of the structures which are involved in the normal functioning or activity of the brain and the abnormal functioning manifesting in psychiatric, behavioral and addiction disorders.

Accordingly, the present invention relates to modulation of neuronal activity to affect psychological or psychiatric activity. The present invention finds particular application in the modulation of neuronal function or processing to effect a functional outcome. The modulation of neuronal function is particularly useful with regard to the prevention, treatment, or amelioration of psychiatric, psychological, conscious state, behavioral, mood, and thought activity (unless otherwise indicated these will be collectively referred to herein as "psychological activity" or "psychiatric activity"). When referring to a pathological or undesirable condition associated with the activity, reference may be made to "psychiatric disorder" or "psychological disorder" instead of psychiatric or psychological activity. Although the activity to be modulated usually manifests itself in the form of a disorder such as a mood disorder (e.g., major depressive disorder, bipolar disorder, and dysthymic disorder) or an anxiety disorder (e.g., panic disorder, posttraumatic stress disorder, obsessive-compulsive disorder and phobic disorder), one skilled in the art appreciates that the invention may also find application in conjunction with enhancing or diminishing any neurological or psychiatric function, not just an abnormality or disorder. Psychiatric activity that may be modulated can include, but not be limited to, normal functions such as alertness, conscious state, drive, fear, anger, anxiety, repetitive behavior, impulses, urges, obsessions, euphoria, sadness, and the fight or flight response.

The present invention finds particular utility in its application to human psychological or psychiatric activity/disorder. One skilled in the art appreciates that the present invention is applicable to other animals which exhibit behavior that is modulated by the brain. This may include, for example, primates, canines, felines, horses, elephants, dolphins, etc. Utilizing the various embodiments of the present invention, one skilled in the art may be able to modulate the functional outcome of the brain to achieve a desirable result.

One technique that offers the ability to affect neuronal function is the delivery of electrical and/or chemical stimulation for neuromodulation directly to target tissues via an implanted device having a probe. The probe can be a stimulation portion, an electrode, a stimulation lead or electrode assembly or drug-delivery catheter. The electrode assembly may be one electrode, multiple electrodes, or an array of electrodes in or around the target area. The proximal end of the probe is coupled to system to operate the device to stimulate the target site. Thus, the probe is coupled to a pulse generating source or a signal generating source, for example, an electrical signal source, pharmaceutical delivery pump, or both which, in turn, is operated to stimulate the predetermined treatment site. In certain embodiments, the probe can be incorporated into the device such that the probe and the signal generating device are a single unit.

Thus, certain embodiments of the present invention involve a method of treating a mood and/or anxiety disorder comprising the steps of: surgically implanting an electrode or a stimulation portion, wherein after implantation the electrode or stimulation portion is in communication with a predetermined site; coupling the electrode or stimulation portion to a pulse generating source or generator; and generating a signal to modulate the predetermined site thereby treating the mood and/or anxiety disorder.

In further embodiments, neuromodulation of the predetermined site of the present invention can be achieved using magnetic stimulation. One such system that can be employed and that is well known in the art is described in U.S. Pat. No. 6,425,852.

The therapeutic system or deep brain system of the present invention is surgically implanted as described in the above sections. One of skill in the art is cognizant that a variety of electrodes or electrical stimulation leads may be utilized in the present invention. It is desirable to use an electrode or lead that contacts or conforms to the target site for optimal delivery of electrical stimulation. One such example, is a single multi contact electrode with eight contacts separated by 2½ mm each contract would have a span of approximately 2 mm. Another example is an electrode with two 1 cm contacts with a 2 mm intervening gap. Yet further, another example of an electrode that can be used in the present invention is a 2 or 3 branched electrode/catheter to cover the predetermined site or target site. Each one of these three pronged catheters/electrodes have four contacts 1-2 mm contacts with a center to center separation of 2 of 2.5 mm and a span of 1.5 mm. Similar designs with catheters to infuse drugs with single outlet pore at the extremities of these types of catheters or along their shaft may also be designed and used in the present invention.

Still further, the present invention extends to methods of transplanting cells into a predetermined site to treat mood and/or anxiety disorders. It is envisioned that the transplanted cells can replace damaged, degenerating or dead neuronal cells, deliver a biologically active molecule to the predetermined site or to ameliorate a condition and/or to enhance or stimulate existing neuronal cells. Such transplantation methods are described in U.S. application No. US20040092010.

Cells that can be transplanted can be obtained from stem cell lines (i.e., embryonic stem cells, non-embryonic stem cells, etc.) and/or brain biopsies, including tumor biopsies, autopsies and from animal donors. (See U.S. application No. US20040092010; U.S. Pat. Nos. 5,735,505 and 6,251,669; Temple, Nature Reviews 2:513-520 (2000); Bjorklund and Lindvall, Nat. Neurosci. 3:537-544 (2000)). Brain stem cells can then be isolated (concentrated) from non-stem cells based on specific "marker" proteins present on their surface. In one such embodiment, a fluorescent antibody specific for such a marker can be used to isolate the stem cells using fluorescent cell sorting (FACS). In another embodiment an antibody affinity column can be employed. Alternatively, distinctive morphological characteristics can be employed.

Alternatively, affective disorders can be treated by utilizing other known methods to alter the neuronal activity of the predetermined sites. For example, lesioning and mechanical disruption can be used as described by U.S. Pat. Nos. 6,629,973, and 3,653,385.

In certain embodiments, the predetermined site or target area is the hypothalamus. The hypothalamus consists of gray matter nuclei that surrounds the anterior end of the third ventricle. The hypothalamus is grouped into three levels that are also grouped into three medial to lateral zones, i.e., (front to back) chiasmatic (i.e., suprachiasmatic, paraventricular, anterior, supraoptic, and lateral and medial preoptic nuclei), tuberal (i.e., dorsomedial, ventromedial, arcuate, and tuberal nuclei), and posterior (medial and lateral mamillary and posteriour nuclei). The hypothalamus integrates internal and external stimuli that is received via afferent pathways and relays or projects output via efferent pathways. Exemplary afferent pathways to the hypothalamus, include, but are not limited to input from the brain stem via dorsal longitudinal fasciculus, medial forebrain bundle, and mamillary peduncle; inputs from the thalamus via the inferior thalamic peduncle, input from the hippocampus via the fornix, inputs from the amygdala via the stria terminalis, input from the cerebral cortex via the medial forebrain bundle, and direct input from the eyes and olfactory bulb. Exemplary efferent pathways to the hypothalamus, include, but are not limited to output from the septal area and nuclei via the medial forebrain bundle; output from the anterior nucleus of the thalamus via the mamillothalamic tract; output from the mediodorsal nucleus of the thalamus via the inferior thalamic peduncle; output from the amygdaloid complex via the stria terminalis and the ventral amygdalopetal pathway; output from the brainstem nuclei and spinal cord via the dorsal longitudinal fasciculsus; output from the adenohypophysis via the tuberohypophyseal tract and hypophyseal portal system; and output from the neurohypophysis via the supraopticohypophyseal tract. Thus, one skill in the art is cognizant that the scope of the present invention includes all the associated gray matter nuclei of the hypothalamus, as well as any afferent and/or efferent projections, which would include any myelinated and/or non-myelinated projections of the hypothalamus. Stimulation of the hypothalamus and/or any myelinated and/or non-myelinated projections of the hypothalamus can result in changes that alleviate or improve the mood and/or anxiety disorder of the subject. It is contemplated that modulating the hypothalamus and/or myelinated and/or non-myelinated projections of the hypothalamus via electrical and/or chemical stimulation can result in increasing, decreasing, masking, altering, overriding or restoring neuronal activity resulting in treatment of the mood and/or anxiety disorder. It is envisioned that a possible mechanism by which stimulation of the hypothalamus may affect a mood and/or anxiety disorder may be via modulation of the neuroendocrine axis. It is envisioned that stimulating the hypothalamus and/or any myelinated and/or non-myelinated projections of the hypothalamus may influence the neuroendocrine axis thereby affecting mood and/or anxiety disorders. A neuroendocrine disturbance that has been shown to be associated with depression is a hypersecrection of cortisol from the adrenal cortex in response to excessive or hypersecretion of adrenocorticotropin (ATCH) from the pituitary. The hypersecretion of ATCH is in response to an excessive or hypersecretion of corticotropin-releasing hormone (CTRH) from the hypothalamus. Thus, it is envisioned that stimulating the hypothalamus or related projections may modulate the hypersecretion of cortisol or any other neuroendocrine disturbance. Another possible mechanism by which stimulation of the hypothalamus may affect a mood and/or anxiety disorder may be via modulation of the hypothalamic-limbic circuits, for example, but not limited to the circuit of Papez (Goetz, Textbook of Clinical Neurology, $2^{nd}$ ed., pp. 64-65 2003 and Brodal, p. 672, Neuroanatomy $3^{rd}$ ed).

In further embodiments, the predetermined site or target area is the inferior thalamic peduncle (ITP). Stimulation of ITP and/or the surrounding or adjacent white matter tracts leading to or from the ITP or white matter tracts that are contiguous with ITP results in changes that alleviate or improve the mood and/or anxiety disorder of the subject. It is contemplated that modulating ITP and/or surrounding or adjacent or contiguous white matter tracts leading to or from the ITP via electrical and/or chemical stimulation can result in increasing, decreasing, masking, altering, overriding or restoring neuronal activity resulting in treatment of the mood and/or anxiety disorder. It is envisioned that the mechanism by which stimulation of the ITP may affect a mood and/or anxiety disorder is via influencing the cortex and/or the brainstem. ITP consists of white matter tracts leading to and from the cortex and brain stem. Thus, stimulation of the ITP may affect the cortex and/or the brainstem thereby affecting the mood and/or anxiety disorders. More specifically, one skill in the art realizes that the ITP or fibers designated as the ITP follow a ventrolaterally-oriented course towards the temporal lobe cortex.

Yet further, the predetermined site or target area is the thalamic reticular nucleus. Thalamic reticular nucleus is classified as one of the diffuse-projection nuclei of the thalamus, which have widespread connections in the cerebral cortex and thalamus. More specifically, the reticular nucleus caps the entire lateral aspect of the thalamus and is separated from the lateral nucleic by the external medullary lamina. The nuclei or cells of the reticular nucleus receives input (also referred to as afferent pathways) from the cerebral cortex, other thalamic nuclei, and brainstem, and then projects information (also referred to as efferent pathways) back to the thalamic nuclei. Thus, stimulation of the thalamic reticular nucleus and/or any myelinated and/or non-myelinated projections of the thalamic reticular nucleus can result in changes that alleviate or improve the mood and/or anxiety disorder of the subject. It is contemplated that modulating the thalamic reticular nucleus and/or myelinated and/or non-myelinated projections of the hypothalamus via electrical and/or chemical stimulation can result in increasing, decreasing, masking, altering, overriding or restoring neuronal activity resulting in treatment of the mood and/or anxiety disorder. It is envisioned that the mechanism by which stimulation of the thalamic reticular nucleus may affect a mood and/or anxiety disorder is via influencing other thalamic nuclei. The reticular nucleus is the only thalamic nucleus that does not have projections to the cortex, and the only thalamic nucleus that has inhibitory output. Thus, stimulation of the thalamic reticular nucleus may affect at least one other thalamic nuclei thereby affecting the mood and/or anxiety disorders.

Using the therapeutic stimulation system of the present invention, the predetermined site or target area is stimulated in an effective amount or effective treatment regimen to decrease, reduce, modulate or abrogate the mood and/or anxiety disorder. Thus, a subject is administered a therapeutically effective stimulation so that the subject has an improvement in the parameters relating to the affective disorder including subjective measures such as, for example, neurological examinations and neuropsychological tests (e.g., Minnesota Multiphasic Personality Inventory, Beck Depression Inventory, Hamilton Rating Scale for Depression, or Yale-Brown Obsessive Compulsive score (Y-BOCS)), motor examination, and cranial nerve examination, and objective measures including use of additional psychiatric medications, such as anti-depressants, or other alterations in blood flow or metabolism in the brain. The improvement is any observable or measurable improvement. Thus, one of skill in the art realizes that a treatment may improve the patient condition, but may not be a complete cure of the disease.

Treatment regimens may vary as well, and often depend on the health and age of the patient. Obviously, certain types of disease will require more aggressive treatment, while at the same time, certain patients cannot tolerate more taxing regimens. The clinician will be best suited to make such decisions based on the known subject's history.

According to one embodiment of the present invention, the target site is stimulated using stimulation parameters such as, pulse width of about 1 to about 500 microseconds, more preferable, about 1 to about 90 microseconds; frequency of about 1 to about 300 Hz, more preferably, about 100 to about 185 Hz; and voltage of about 0.5 to about 10 volts, more preferably about 1 to about 10 volts. It is known in the art that the range for the stimulation parameters may be greater or smaller depending on the particular patient needs and can be determined by the physician. Other parameters that can be considered may include the type of stimulation for example, but not limited to acute stimulation, subacute stimulation, and/or chronic stimulation.

It is envisioned that stimulation of the hypothalamus and/or any myelinated and/or non-myelinated projections of the hypothalamus and/or the ITP and/or the adjacent, surrounding or contiguous white matter tracts of the ITP modulates, and/or the thalamic reticular nucleus and/or any myelinated and/or non-myelinated projections of the thalamic reticular nucleus, or other targets in the limbic-cortical circuit or pathway thereby improving any dysfunctional limbic-cortical circuits resulting in an improvement or alleviation or providing remission of depression and/or anxiety in the treated subjects. Other such improvements can be sensations of calm, tranquility, peacefulness, increased energy and alertness, improved mood, and improvement in motor speed and in spontaneity of speech, decreases in anxiety, decreases in repetitive behavior, impulses, obsessions, etc.

For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether objective or subjective.

Figure 3:
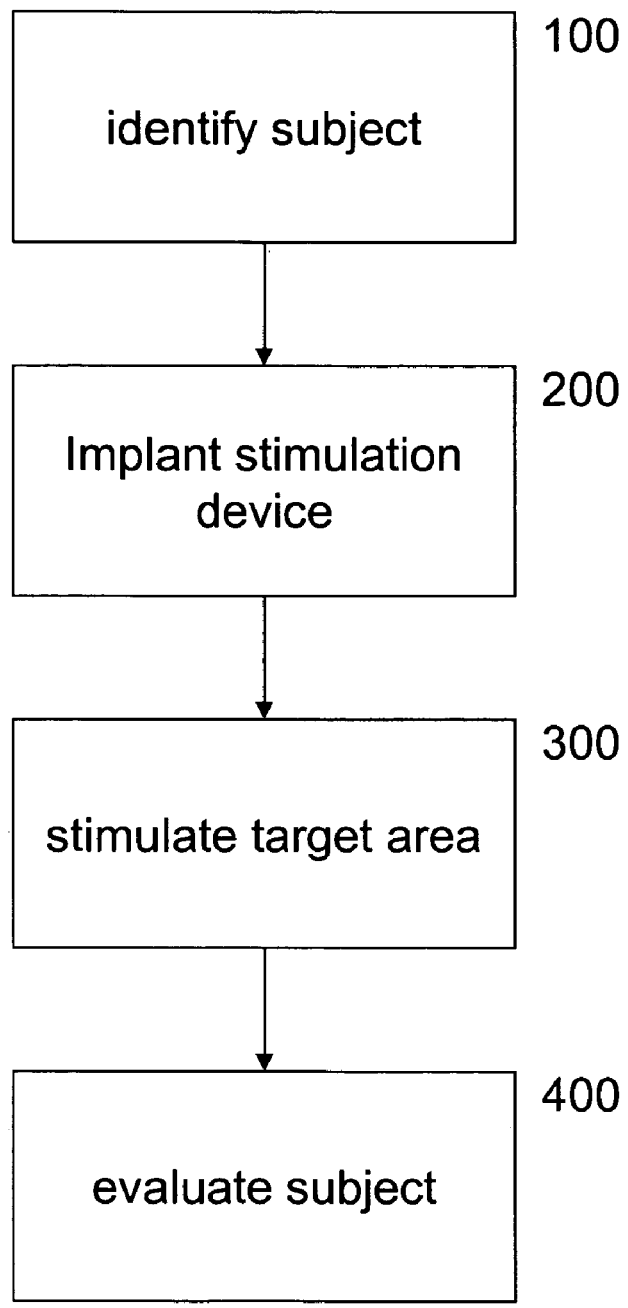
FIG. 3 is a flowchart describing the general procedure.

FIG. 3 summarizes the general procedure of the present invention. Any of the above described methods can be used to identify a subject or diagnose a subject that suffers from an affective disorder (100). Once the subject is identified, a stimulation device is implanted (200) into the subject such that the predetermined area of the subject's brain is stimulated (300). After the target area has been stimulated (i.e., electrical, chemical, thermal magnetic and/or ultrasonic stimulation), the subject is evaluated to determine the change in the affective disorder. One of skill in the art realizes that the present invention is not bound by the described methods or devices and that any method or device that would result in neuromodulation of the predetermined area could be used in the present invention.

VII. COMBINATION TREATMENT

In order to increase the effectiveness of the electrical stimulation method of the present invention, it may be desirable to combine electrical stimulation with chemical stimulation to treat the mood and/or anxiety disease.

In one preferred alternative, an implantable signal generator and electrical stimulating lead and an implantable pump and catheter(s) are used to deliver electrical stimulation and/or one or more stimulating drugs to the above mentioned areas as a treatment for mood and/or anxiety disorders.

Herein, stimulating drugs comprise medications, anesthetic agents, synthetic or natural peptides or hormones, neurotransmitters, cytokines and other intracellular and intercellular chemical signals and messengers, and the like. In addition, certain neurotransmitters, hormones, and other drugs are excitatory for some tissues, yet are inhibitory to other tissues. Therefore, where, herein, a drug is referred to as an "excitatory" drug, this means that the drug is acting in an excitatory manner, although it may act in an inhibitory manner in other circumstances and/or locations. Similarly, where an "inhibitory" drug is mentioned, this drug is acting in an inhibitory manner, although in other circumstances and/or locations, it may be an "excitatory" drug. In addition, stimulation of an area herein includes stimulation of cell bodies and axons in the area.

Similarly, excitatory neurotransmitter agonists (e.g., norepinephrine, epinephrine, glutamate, acetylcholine, serotonin, dopamine), agonists thereof, and agents that act to increase levels of an excitatory neurotransmitter(s) (e.g., edrophonium; Mestinon; trazodone; SSRIs (e.g., flouxetine, paroxetine, sertraline, citalopram and fluvoxamine); tricyclic antidepressants (e.g., imipramine, amitriptyline, doxepin, desipramine, trimipramine and nortriptyline), monoamine oxidase inhibitors (e.g., phenelzine, tranylcypromine, isocarboxasid)), generally have an excitatory effect on neural tissue, while inhibitory neurotransmitters (e.g., dopamine, glycine, and gamma-aminobutyric acid (GABA)), agonists thereof, and agents that act to increase levels of an inhibitory neurotransmitter(s) generally have an inhibitory effect (e.g., benzodiasepine (e.g., chlordiazepoxide, clonazepam, diazepam, lorazepam, oxazepam, prazepam alprazolam); flurazepam, temazepam, or triazolam). (Dopamine acts as an excitatory neurotransmitter in some locations and circumstances, and as an inhibitory neurotransmitter in other locations and circumstances.) However, antagonists of inhibitory neurotransmitters (e.g., bicuculline) and agents that act to decrease levels of an inhibitory neurotransmitter(s) have been demonstrated to excite neural tissue, leading to increased neural activity. Similarly, excitatory neurotransmitter antagonists (e.g., prazosin, and metoprolol) and agents that decrease levels of excitatory neurotransmitters may inhibit neural activity. Yet further, lithium salts and anesthetics (e.g., lidocane) may also be used in combination with electrical stimulation.

In addition to electrical stimulation and/or chemical stimulation, other forms of stimulation can be used, for example magnetic, or thermal, ultrasonic or combinations thereof. Magnetic stimulation can be provided by internally implanted probes or by externally applied directed magnetic fields, for example, U.S. Pat. Nos. 6,592,509; 6,132,361; 5,752,911; and 6,425,852, each of which is incorporated herein in its entirety. Thermal stimulation can be provided by using implanted probes that are regulated for heat and/or cold temperatures which can stimulate or inhibit neuronal activity, for example, U.S. Pat. No. 6,567,696, which is incorporated herein by reference in its entirety.

VIII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Patient Selection for Treatment of Depression

A 49 years old female with history of recurrent depression for 23 years and a 5 years episode of major depression fulfilling DSM IV criteria (depressed mood, anhedonia, late night insomnia, increased appetite, hopeless attitude and suicidal ideas) was presented.

Symptoms were resistant to medication and electroconvulsive therapy. Hamilton, Beck and Zung scales detected high scores for depression. Neuropsychological abnormalities in memory and praxias were also documented.

Example 2

Surgical Procedure

Under local anesthesia, a stereotactic frame was first placed on the patient's head, followed by acquisition of an MRI (Magnetic Resonance Imaging) scan to localize the target region. The patient was then taken to the operating room where, under local anesthesia, burr holes were placed behind the hairline. Two coronal burr-holes were drilled at 15 mm from the midline in each side plus a plastic ring and skull cap (by Medtronic) to hold the electrodes. Guided by TC and MRI the electrodes were directed to coordinates lateral (X)=5.0 mm at each side of the midline, AP (Y)=4.0 mm posterior to anterior commisure (AC), and depth (Z) over passed by 10 mm the anterior commisure to posterior commisure level (AC-PC). The electrodes trajectories were oblique with a 10° inclination in the frontal plane and 20° inclination in the sagittal plane. Temporary eight contacts electrodes were plotted on correspondent frontal sections of the Schaltenbrand and Wahren atlas (Schaltenbrand and Wahren, 1977) (FIG. 3). The electrodes were left externalized for recording and temporary stimulation.

Example 3

Acute Stimulation of a Depressed Patient

After surgery electrical stimulation (ES) of different pair of contacts of the electrodes was carried out using the ES parameters (130 Hz, 0.45 ms) intended for subacute and chronic stimulation increasing the voltage from 1.0 to 10.0 V to detect adverse reactions. Searching for recruiting responses was performed by bipolar stimulation of different pair of contacts at 6 Hz, 1.0 ms and increasing from 0.5 to 4.0 mA while recording scalp EEG in conventional 10-20 montage referred to the ears (A1-A2). Regional DC shifts searched at 60 Hz, 1.0 ms and intensities from 1.0 to 4.0 mA (Velasco et al., 1996).

Figure 4:
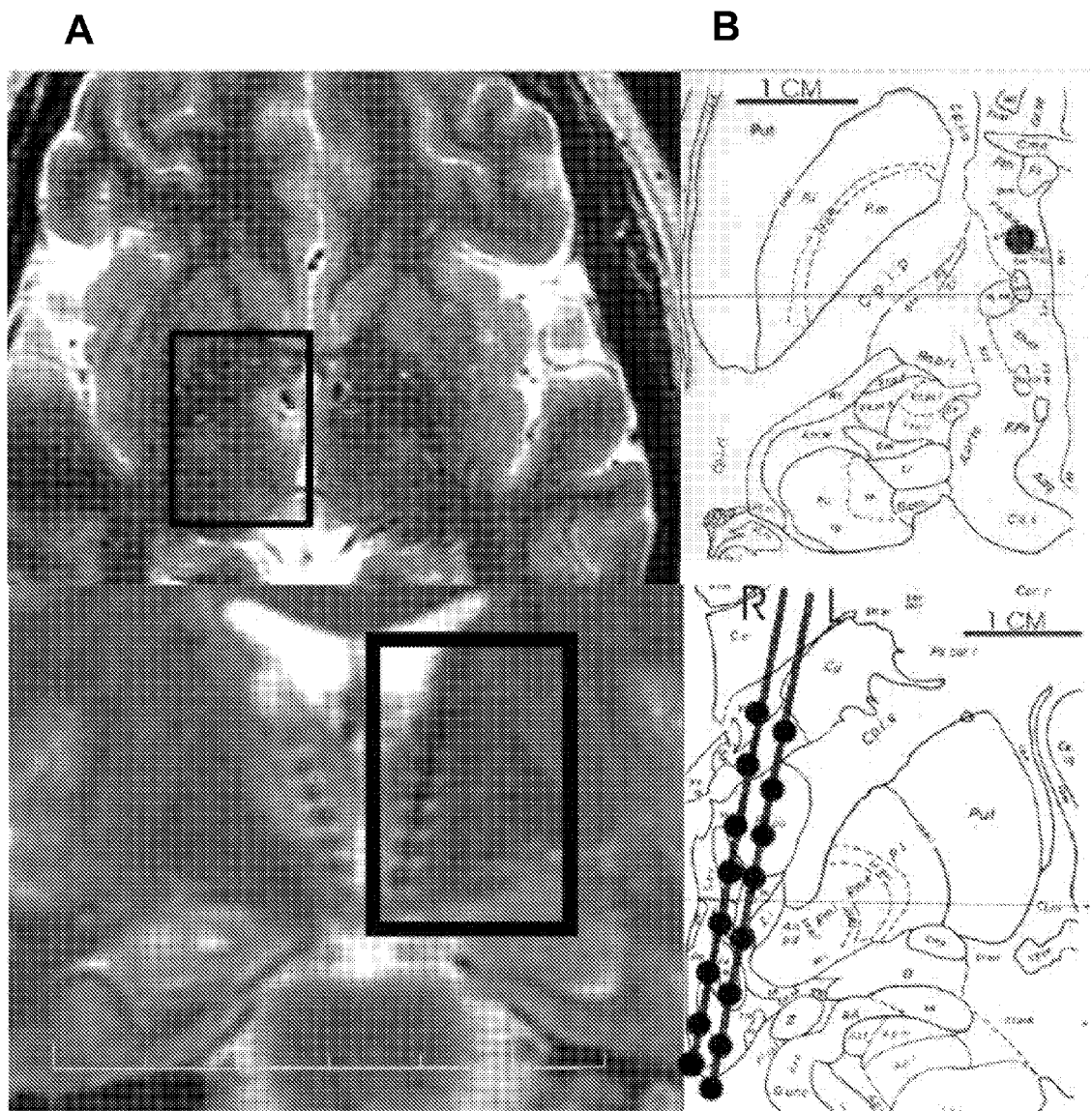
FIGS. 4A and 4B illustrate the placement of the electrodes.
Figure 6:
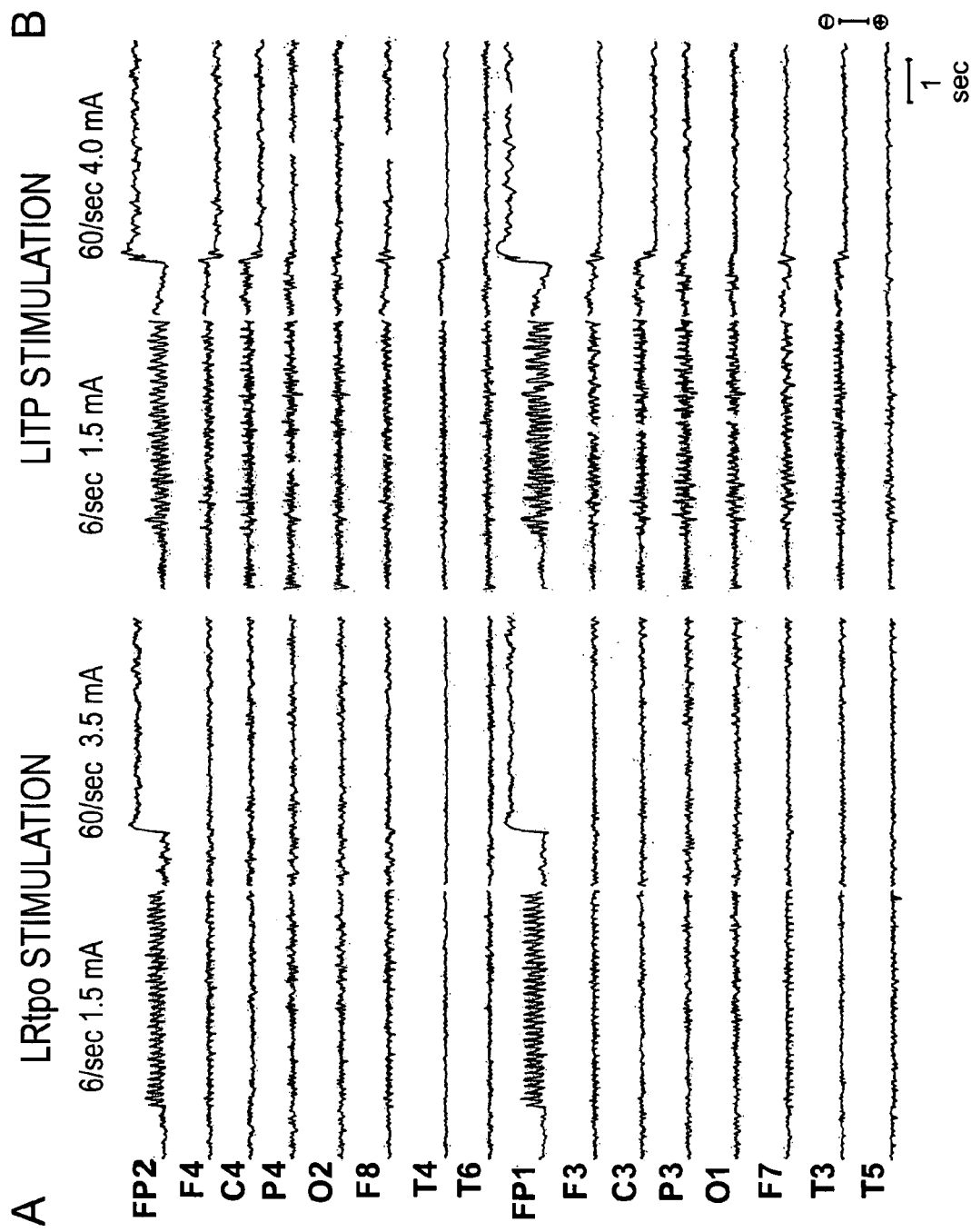
FIGS. 6A and 6B show scalp distribution of the electrocortical responses elicited by acute low frequency (6/sec) and high frequency (60/sec) stimulation of the left nucleus reticularis thalami (L Rtpo) and the left inferior thalamic peduncle (ITP). Conventional EEG recording from right and left frontopolar (FP2, FP1), frontal (F4, F3), central (C4, C3), parietal (P4, P3), occipital (O2, O1), frontotemporal (F8, F7) finally anterior temporal (T4, T3) and posterior temporal (T6, T5) scalp regions referred to ipsilateral ears (A2, A1).

Table I summarizes the effects of low (6Hz) and high (60 Hz) stimulation. Other parameters were 1.0 ms pulse duration, increasing pulse amplitude in steps of 0.5 mA, increasing from 0.5 to 4.0 mA. Stimulation was always unilateral and bipolar between two adjacent contacts of the electrode, that according to our MRI and stereotactic plotting the following structures: 1-2 nucleus ventromedialis hipotalami (Vm), 3-4 fornix (Fx), 5-6 pedunculus thalami inferior (Pd. Th. If) and 7-8 nucleus reticularis polaris (Rtpo) (FIG. 4). While all low frequency stimulation in different pair of contacts elicited RR like potentials and most high frequency stimulation elicited negative DC shifts, the distribution of the cortical responses were different. In Vm, RR were bilateral central and temporal, while DC shifts could not be elicited because at 1.5 mA in right side and 2.0 mA in left side the patient reported and intense sensation of fear that precluded further stimulation. At Fx, RR were recorded in all regions of the ipsilateral EEG and DC shifts were fronto-central ipsilateral. ITP (Pd. Th. If) and Rtpo stimulation at low and high frequencies evoked similar cortical responses prominent at fronto-polar leads in both sides (FIG. 6). Except for the fear sensation reported when stimulating at high frequency the Vm no other objective or subjective reaction were induced up to 4.0 mA.

TABLE 1

Acute Electrical Stimulation

| CONTACTS | FREQUENCY | PULSE AMPLITUDE (mA) Right | PULSE AMPLITUDE (mA) Left | RESPONSE |
|---|---|---|---|---|
| 1-2 (VmH) | 6 for RR | 2.5 | 2.5 | Bilarteral central and temporal |
|  | 60 for DC shift | 1.5 | 2.0 | Intense fear and anxiety |
| 3-4 (Fx) | 6 for RR | 4.0 | 4.0 | Ipsilateral Generalized |
|  | 60 for DC shift | 2.0 | 2.5 | Ipsilateral fronto central |
| 5-6 (ITP) | 6 for RR | 3.0 | 2.5 | Bilateral fronto polar |
|  | 60 for DC shift | 4.0 | 1.5 | Bilateral fronto polar |
| 7-9 (Rtpo) | 60 for RR | 2.5 | 1.5 | Bilateral fronto polar |
|  | 60 for DC shift | 4.0 | 3.5 | Bilateral fronto polar |

Example 4

Subacute Stimulation of a Depressed Patient

Figure 5:
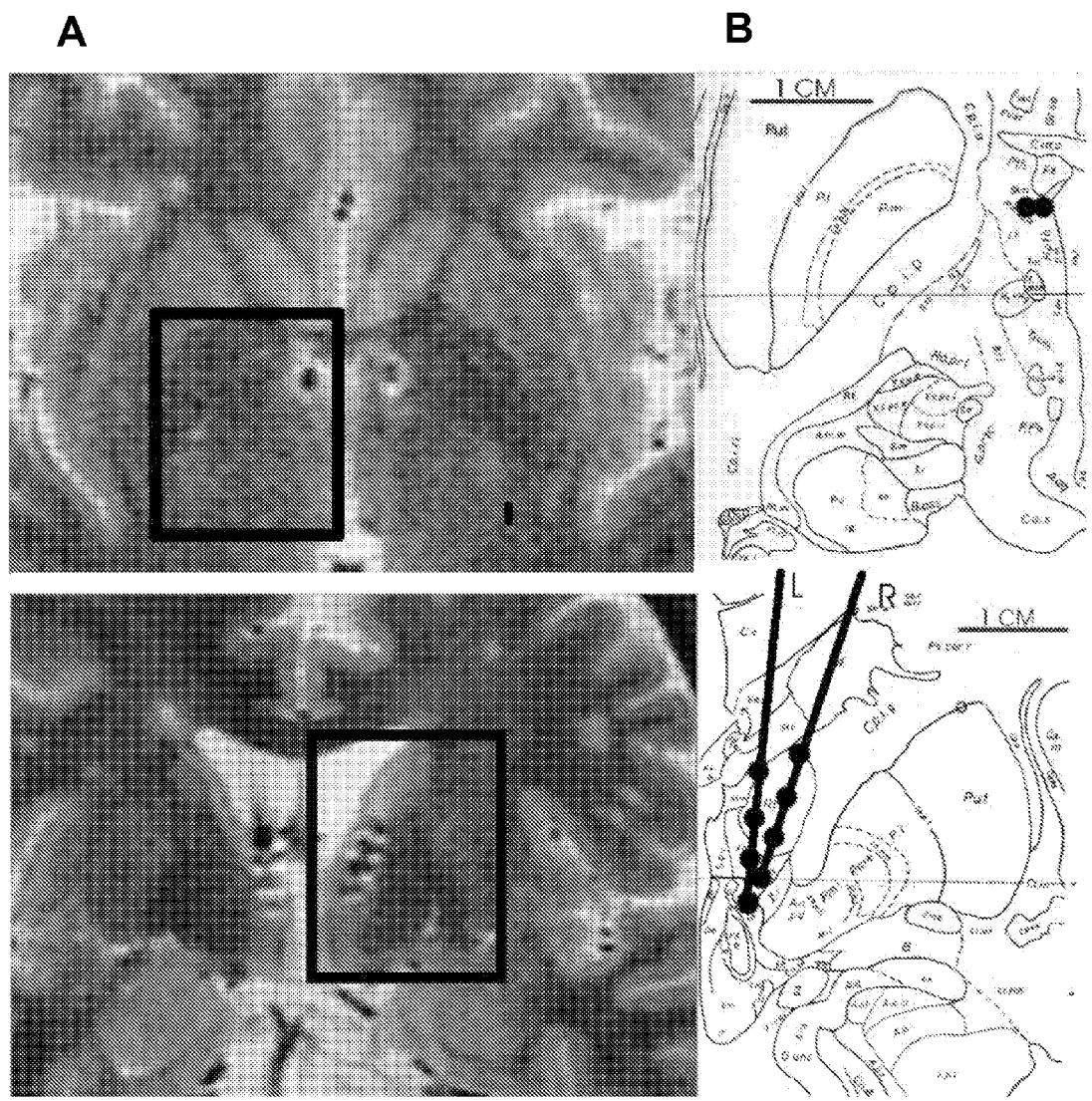
FIGS. 5A and 5B show an MRI and plotting of electrodes for chronic stimulation indicating the place for stimulation. As in FIG. 4B, the abbreviations are the same.

Stimulation was always bipolar between two adjacent contacts. This stimulation circumscribed the electrical current on a specific target. The most efficient contacts i.e., the ones that induced the best clinical response in acute stimulation test at the lowest threshold and were not accompanied by adverse reactions, were selected for a 30 days trial of continuous stimulation. The patient remained hospitalized during that period and EEG recordings, depression scales and neuropsychological evaluations were repeated every week. At the end of this period, the patient was taken back to the operating room, and under general anesthesia the stereotactic frame was repositioned, the 8 contact electrodes were removed and tetrapolar electrodes (DBS 3389) with intercontact distance of 1.5 mm were aimed to the site where most efficient stimulation was obtained. The electrodes were internalized and connected through extension cables to a dual IPG (Kinetra by Medtronic) (FIG. 5).

The initial improvement in depression scales described above was further increased by bilateral continuous stimulation through contacts 5-6 (ITP). HAM-D decreased one month later, to 4, BDI to 11 and ZDS to 35. From the neuropsychological evaluation visual attention, visuo-constructive perception and verbal fluency were normal in the BL and remained so. All abnormal neuropsychological findings in BL were improved at one month post stimulation: Abstraction that was mildly impaired (Wisconsin Card Sorting Test) in BL (6 categories, 60 correct, 45 errors) improved substantially (6 categories, 60 correct and 20 errors). Manual praxias were severely affected mainly on right hand and improved in both sides mainly on the right. Hemispheric dominance (Finger Tapping Test) affected mainly on the right side with scores of 2.87 tap/s on the right and 3.67 tap/s on the left became better for right hand (5.63 tap/s and 5.28 tap/s in right and left respectively). Mild verbal memory deficit (Rey Test) (7 trials to learn 10 words in 8 min 10 s time became 5 trials in 4 min 51 s). Finally, non verbal memory (Corsi Block Tapping Test) shown moderate deficit (21 trials=8 correct+13 errors in 6 min 54 s) became light memory problem (18 trials=12 correct +6 errors in 4 min 18 s).

in 3 conditions for the patient: Baseline (prior surgical procedure), the lowest score obtained during the follow up (best condition) and the highest score obtained in the follow up (worst condition). Items in SCL-90 scale were evaluated from 0=(non existent) to 4 (maximal intensity), so higher scores indicate more severe dysfunction. AVG is the average of all the items for each evaluation, that closely corresponded to the GAF score.

TABLE 2

|  | SCL 90 | | | | | | | | | |
| --- | --- | --- | --- | --- | --- | --- | --- | --- | --- | --- |
|  | SOM | OC | IS | DEP | ANX | HOS | PHOB | PAR | AVG | GAF |
| Baseline | 1.6 | 2.6 | 2.8 | 3.5 | 1.6 | 2.0 | 1.3 | 0.7 | 2.0 | 20 |
| Best Condition | 0.2 | 0.3 | 0.4 | 0.2 | 0.5 | 0.2 | 0.0 | 0.2 | 0.2 | 90 |
| Worst Condition | 2.0 | 0.4 | 1.3 | 0.9 | 1.4 | 0.8 | 0.1 | 1.3 | 1.1 | 60 |

Abbreviations:
SOM—Somatization;
O-C—Obsessive-Compulsive;
I-S—Interpersonal Sensitivity;
DEP—Depression;
ANX—Anxiety;
HOS—Hostility;
PHOB—Phobic Anxiety; and
PAR—Paranoid Ideation;
GAF—global assessment of functioning.

Example 5

Chronic Stimulation of a Depressed Patient

The patient was discharged from the hospital and bipolar stimulation between contacts 0 (positive) and 1 (negative) in both sides, setting the parameters at 130 Hz 0.45 ms and 2.0 and 2.5 V amplitude in the left and right sides, respectively. All ATD medication was discontinued and appointments for monthly follow-up were scheduled. In each visit, the patient had a psychiatric and neuropsychological evaluations through the same scales used in BL and a repeated EEG. Every month recording of RR induced by stimulation through the IPG at 6 Hz, 0.45 ms and 6.0 to 8.0 V, were performed for monitoring the integrity of the stimulation systems as well as the efficiency of stimulation (Velasco et al., 1998). At month 8, the patient entered a double blind protocol with stimulation off for 2 months.

Figure 7:
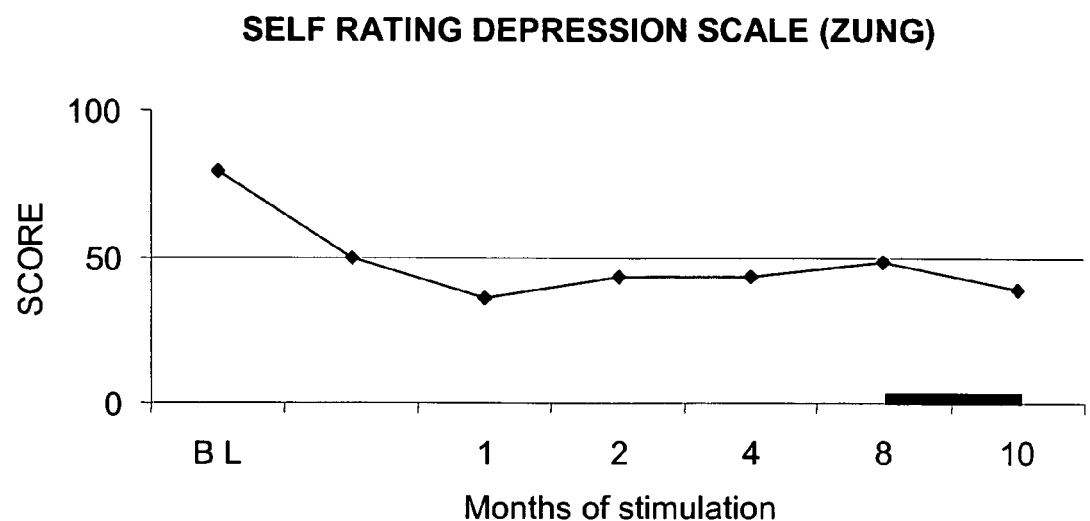
FIGS. 7A and 7B show the results of the Self Rating Depression Scale (ZDS) and the Depression Scale of Beck (BDI) and Hamilton (HAM-D).
Figure 7:
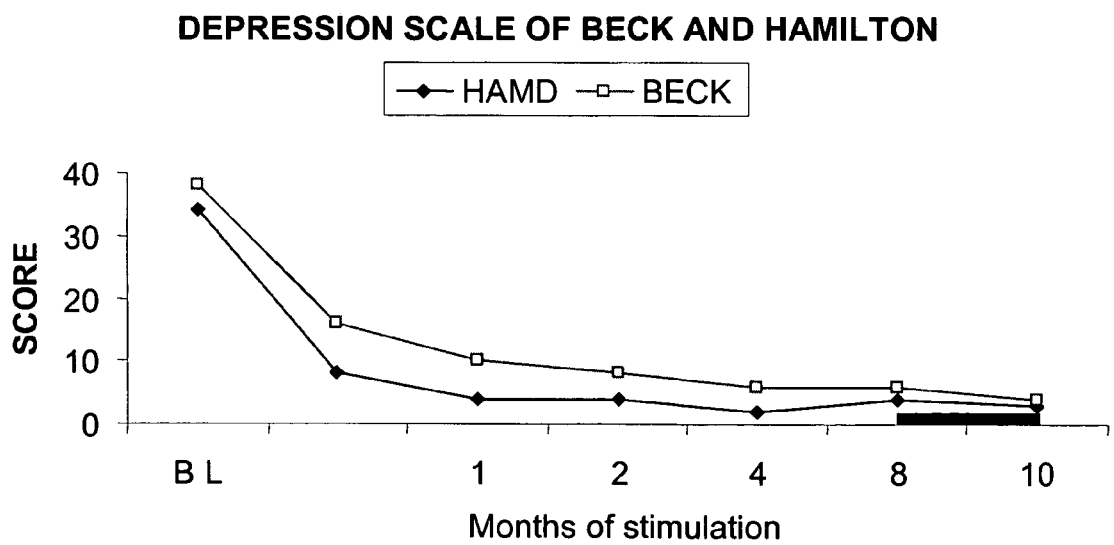
Figure 8:
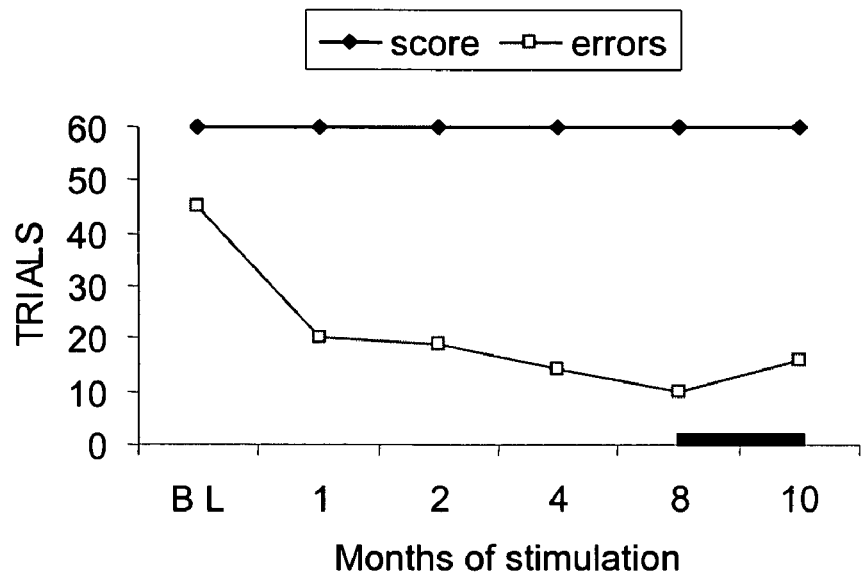
FIGS. 8A-8D show neuropsychological testing after ITP-DBS.
Figure 8:
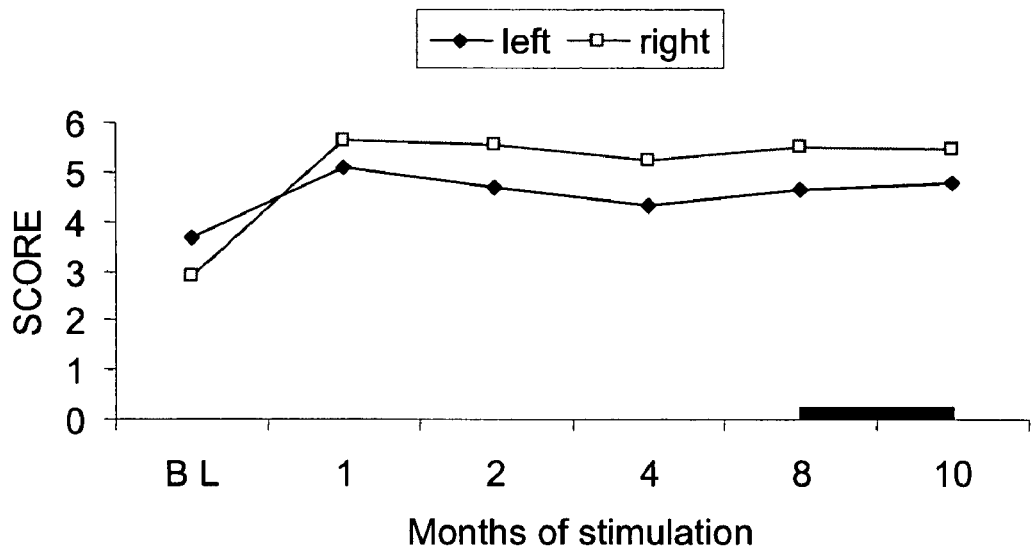
Figure 8:
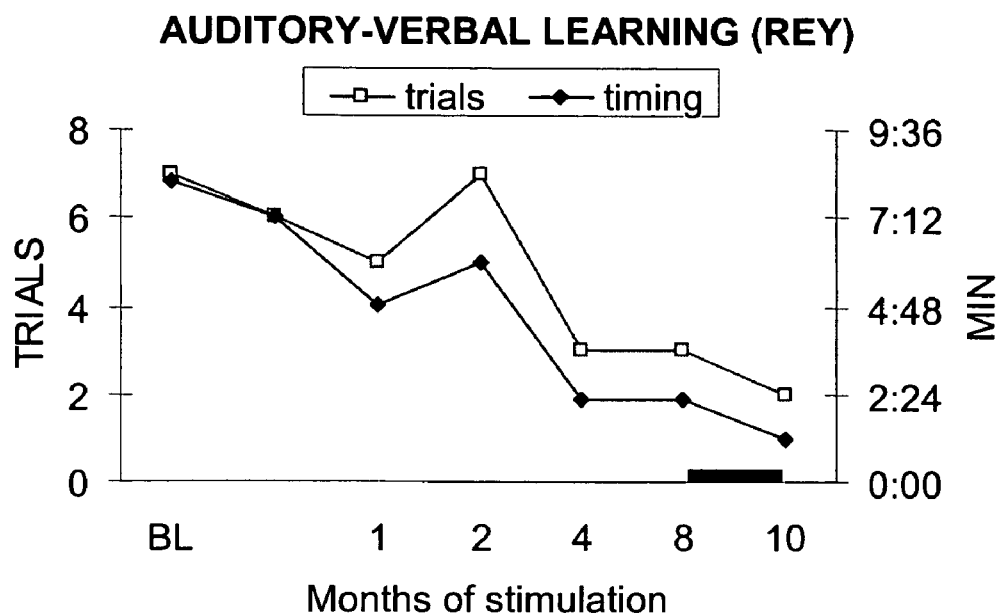
Figure 8:
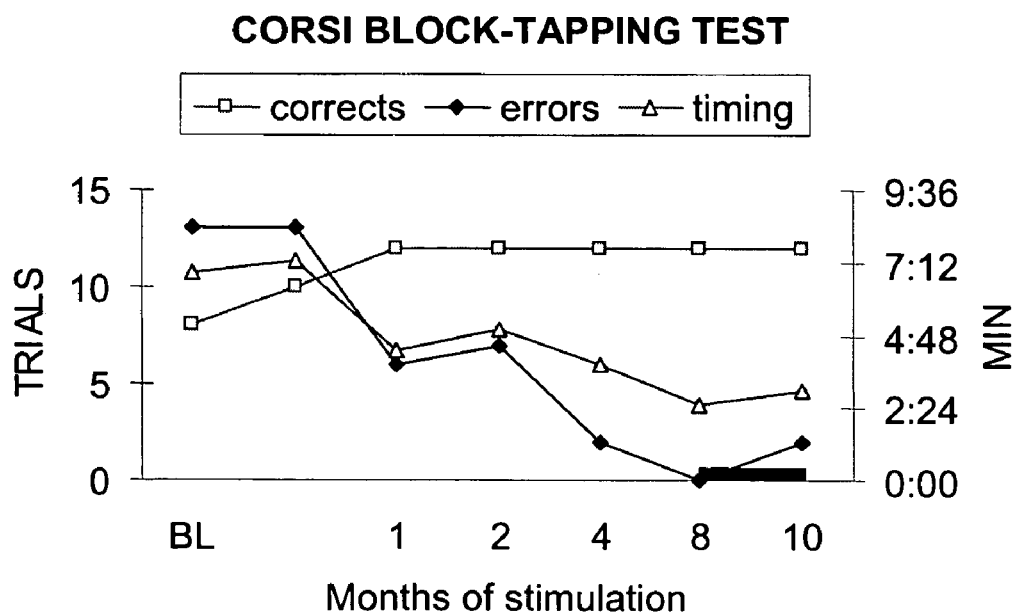

The patient has remained without ATD with reduction in all depression scales scores and improvement in the verbal and non verbal memory and abstraction test that became normal by month 8 (FIG. 7 and FIG. 8). At this time a double blind protocol started with patient and examiners (psychiatrist and neuropsychologist) unaware of the stimulator being turned off and only one monitor handling the code. The double blind test was valid because the patient had not objective or subjective sensation when stimulation was on. During double-blind period the patient remained in complete remission of depression (HAM-D below 7 points). Patient has returned to home work and her relatives describe her as the active and pleasant person she used to be many years before.

Figure 9:
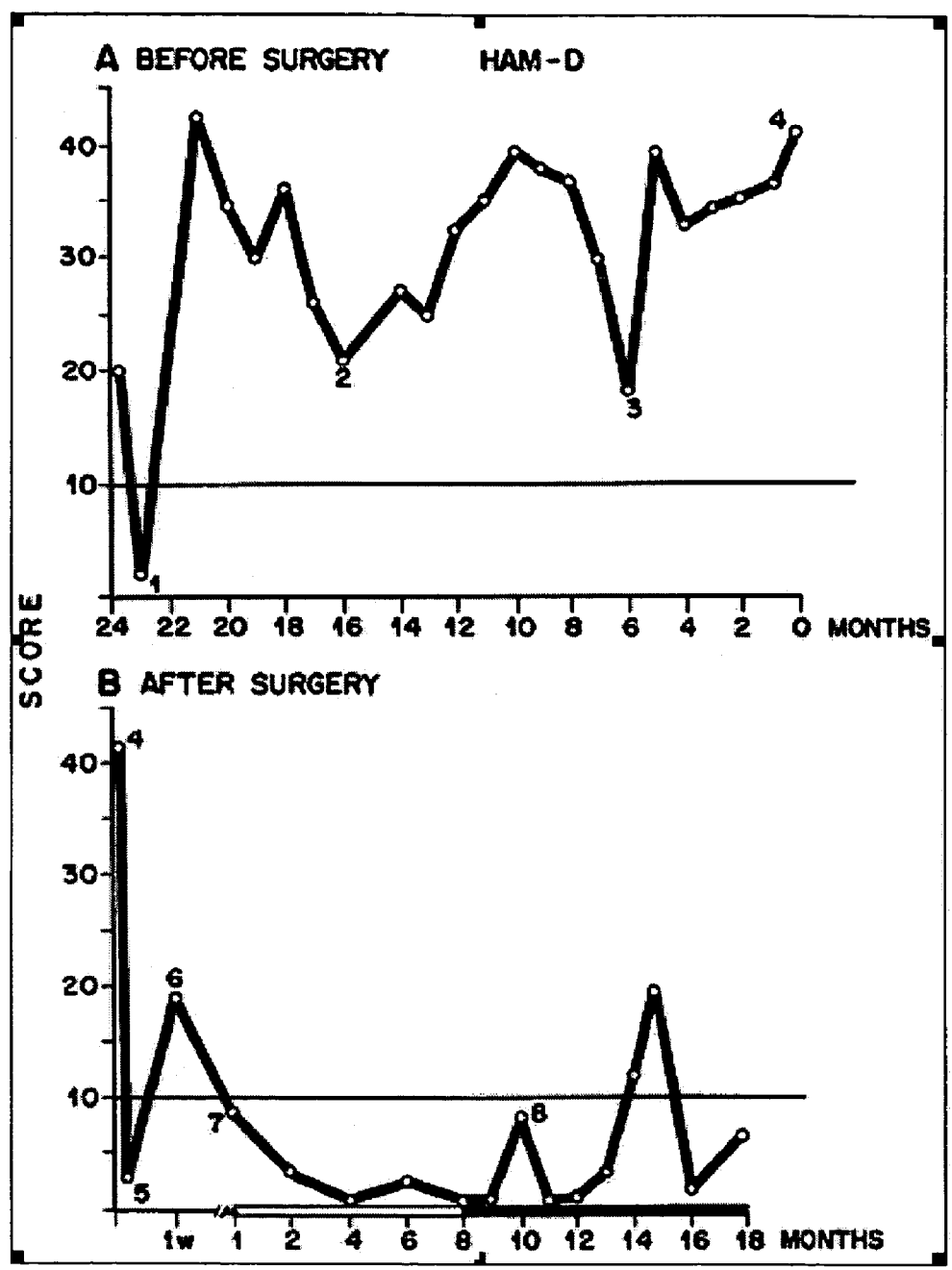
FIGS. 9A and 9B show HAM-D score throughout follow-up of the reported case.

FIG. 9A and FIG. 9B represents a summary of the HAM-D scores for the patient before and after the surgery.

Table 2 the Symptom Checklist 90 (SCL90) scores obtained for the patient. The SCL-90 scores were obtained

Example 6

Treatment of Obsessive-Compulsive Disorder

A 21 years old male with a 15 year history of obsessive-compulsive disorder characterized by agoraphobia and compulsive writing of his symptoms and resistant to pharmacological and cognitive therapy with a score of 36 in Yale-Brown Obsessive Compulsive score (Y-BOCS) underwent the surgery protocol as described in Example 2.

Prior to surgery a complete neurophyshological evaluation was performed. Electrodes (DBS 3389 by Medtronic) were sterotactically implanted in the ITP area (see Table 3) and their correct position confirmed by MRI and electrophysiologically by the evoked recruiting responses.

TABLE 3

| STEREOTACTIC LOCALIZATION OF STIMULATED CONTACTS | | | | | | |
| --- | --- | --- | --- | --- | --- | --- |
| PATIENT | CA-CP | SIDE | POLE | X* | Y* | Z* |
| SW10 | 25.3 | R | + | 3.9 | 6.4 | 0.5 |
|  |  | L | + | 3.9 | 6.4 | −0.4** |
|  |  | R | − | 5.5 | 3.8 | 2.9 |
|  |  | L | − | 4.9 | 3.5 | 4.5 |

*The x, y, and z stereotactic coordinates are in mm and length of AC-PC line for different cases.
**Negative (−) symbols in front of the numbers indicate the placement below the AC-PC plane for z coordinate.

ES parameters were 130 Hz, with a pulse width of 0.45 ms and a voltage from 2.5 to 4.5 volt, bipolar and continuous. Psychiatric and neuropsychological evaluations were repeated every 3 months.

On the Y-BOCS scale score, the patient decreased more than 20 points and has remained so for 9 months (dropped from 36 to 12), with an improvement in WCST performance from 2 to 6 categories and number of errors decreased from 11 to 34.

Table 4 shows the Symptom Checklist 90 (SCL90) scores obtained for the patient. The SCL-90 scores were obtained in 3 conditions for the patient: Baseline (prior surgical procedure), the lowest score obtained during the follow up (best condition) and the highest score obtained in the follow up (worst condition). Items in SCL-90 scale were evaluated from 0=(non existent) to 4 (maximal intensity), so higher scores indicate more severe dysfunction. AVG is the average of all the items for each evaluation, that closely corresponded to the GAF score. Thus, in view of the data, the stimulation system of the present invention lessened the symptoms of OC, depression, anxiety, etc. and resulted in an increase in general well being as indicated by the increase in GAF.

TABLE 4

SCL 90

|  | SOM | OC | IS | DEP | ANX | HOS | PHOB | PAR | AVG | GAF |
|---|---|---|---|---|---|---|---|---|---|---|
| Baseline | 2.4 | 2.4 | 2.3 | 3.0 | 3.3 | 2.3 | 4.0 | 2.8 | 2.8 | 20 |
| Best Condition | 0.4 | 0.5 | 0.7 | 0.8 | 0.7 | 0.0 | 0.6 | 0.7 | 0.6 | 90 |
| Worst Condition | 1.4 | 2.9 | 2.3 | 2.6 | 2.4 | 0.5 | 2.4 | 2.0 | 2.1 | 40 |

Abbreviations:
SOM—Somatization;
O-C—Obsessive-Compulsive;
I-S—Interpersonal Sensitivity;
DEP—Depression;
ANX—Anxiety;
HOS—Hostility;
PHOB—Phobic Anxiety; and
PAR—Paranoid Ideation Example 7

Treatment of Obsessive-Compulsive Disorder

Three additional patients, as shown in Table 5, suffering from obsessive-compulsive disorder underwent the surgery protocol as described in Example 2. Patient SW7 had a score of 29 in Yale-Brown Obsessive Compulsive score (Y-BOCS), and patients SW14 and SW15 each had a score of 40 in the Yale-Brown Obsessive Compulsive score (Y-BOCS).

TABLE 5

| PATIENT | AGE | SEX | Y-BOCS |
|---|---|---|---|
| SW7 | 34 | M | 29 |
| SW14 | 26 | M | 40 |
| SW15 | 38 | F | 40 |

Prior to surgery a complete neurophyschological evaluation was performed. Electrodes (DBS 3389 by Medtronic) were sterotactically implanted in ITP area (see Table 6) and their correct position confirmed by MRI and electrophysiologically by the evoked recruiting responses.

TABLE 6

STEREOTACTIC LOCALIZATION OF STIMULATED CONTACTS

| Patient | CA-CP | SIDE | POLE | X* | Y* | Z* |
|---|---|---|---|---|---|---|
| SW7 | 24 | R | + | 7.1 | 6.0 | 2.1 |
|  |  | L | + | 6.8 | 6.8 | 3.0 |

TABLE 6-continued

STEREOTACTIC LOCALIZATION OF STIMULATED CONTACTS

| Patient | CA-CP | SIDE | POLE | X* | Y* | Z* |
|---|---|---|---|---|---|---|
|  |  | R | − | 5.3 | 5.3 | 4.6 |
|  |  | L | − | 5.9 | 5.9 | 5.5 |
| SW14 | 24.5 | R | + | 4.5 | 4.1 | −0.2** |
|  |  | L | + | 9.0 | 6.6 | 0.3 |
|  |  | R | − | 5.5 | 3.3 | 2.7 |
|  |  | L | − | 9.3 | 5.0 | 3.3 |
| SW15 | 23 | R | + | 5.8 | 0.5 | −0.2** |
|  |  | L | + | 5.0 | 1.1 | 0.1 |

TABLE 6-continued

STEREOTACTIC LOCALIZATION OF STIMULATED CONTACTS

| Patient | CA-CP | SIDE | POLE | X* | Y* | Z* |
|---|---|---|---|---|---|---|
|  |  | R | − | 5.8 | 0.9 | 2.8 |
|  |  | L | − | 5.5 | 0.9 | 3.1 |

*The x, y, and z stereotactic coordinates are in mm and length of AC-PC line for different cases.
**Negative (−) symbols in front of the numbers indicate the placement below the AC-PC plane for z coordinate.

ES parameters were 130 Hz, with a pulse width of 0.45 ms and a voltage from 2.5 to 4.5 volt, bipolar and continuous. Psychiatric and neuropsychological evaluations were repeated every 3 months.

On the Y-BOCS scale score, the patient SW7 decreased from 29 to 17, the patient SW14 decreased from a score of 40 to 17, while patient SW15 decreased from a score of 40 to 36.

Table 7 shows the Symptom Checklist 90 (SCL90) scores obtained for the patient. The SCL-90 scores were obtained in 3 conditions for the patient: Baseline (prior surgical procedure), the lowest score obtained during the follow up (best condition) and the highest score obtained in the follow up (worst condition). Items in SCL-90 scale were evaluated from 0=(non existent) to 4 (maximal intensity), so higher scores indicate more severe dysfunction. AVG is the average of all the items for each evaluation, that closely corresponded to the GAF score.

TABLE 7

| | \multicolumn{9}{c}{SCL 90} | |
| --- | --- | --- | --- | --- | --- | --- | --- | --- | --- | --- |
| | SOM | OC | IS | DEP | ANX | HOS | PHOB | PAR | AVG | GAF |
| Patient SW7 | | | | | | | | | | |
| Baseline | 1.1 | 1.7 | 0.6 | 1.4 | 1.4 | 0.8 | 0.7 | 0.8 | 1.1 | 40 |
| Best Condition | 0.9 | 0.9 | 0.6 | 1.2 | 0.6 | 0.8 | 0.4 | 0.8 | 0.8 | 70 |
| Worst condition | 1.5 | 1.3 | 1.1 | 1.5 | 1.3 | 1.3 | 1.1 | 1.2 | 1.3 | 40 |
| Patient SW14 | | | | | | | | | | |
| Baseline | 1.4 | 2.7 | 3.0 | 3.1 | 3.2 | 1.7 | 2.3 | 3.3 | 2.6 | 40 |
| Best Condition | 0.9 | 1.6 | 1.3 | 2.0 | 2.5 | 1.8 | 1.1 | 2.5 | 1.7 | 70 |
| Worst Condition | 2.3 | 2.3 | 3.1 | 2.8 | 2.5 | 1.7 | 2.4 | 3.0 | 2.5 | 40 |
| Patient SW15 | | | | | | | | | | |
| Baseline | 3.5 | 3.1 | 1.8 | 4.0 | 3.3 | 2.2 | 3.4 | 1.3 | 2.8 | 20 |
| Best Condition | 2.6 | 2.8 | 0.6 | 3.1 | 3.3 | 1.3 | 0.6 | 0.8 | 1.9 | 50 |
| Worst Condition | 2.1 | 3.0 | 0.4 | 3.7 | 1.9 | 0.7 | 2.1 | 0.7 | 1.8 | 40 |

Abbreviations:
SOM—Somatization;
O-C—Obsessive-Compulsive;
I-S—Interpersonal Sensitivity;
DEP—Depression;
ANX—Anxiety;
HOS—Hostility;
PHOB—Phobic Anxiety; and
PAR—Paranoid Ideation

REFERENCES

All patents and publications mentioned in the specifications are indicative of the levels of those skilled in the art to which the invention pertains. All patents and publications are herein incorporated by reference to the same extent as if each individual publication was specifically and individually indicated to be incorporated by reference.
Bjorklund and Lindvall, Nat. Neurosci. 3:537-544 (2000)
Drevets et al., Nature 386:824-7, 1997.
Ebmeier et al., Br J Psychiatry, 170:77-81, 1997.
Galynker et al., J Nucl Med., 39:608-12, 1998.
Temple, Nature Reviews 2:513-520 (2000)
U.S. application No. US20040092010
U.S. Pat. No. 3,653,385
U.S. Pat. No. 3,731,681
U.S. Pat. No. 3,951,147
U.S. Pat. No. 4,692,147
U.S. Pat. No. 4,772,263
U.S. Pat. No. 5,263,480
U.S. Pat. No. 5,299,569
U.S. Pat. No. 5,423,877
U.S. Pat. No. 5,470,846
U.S. Pat. No. 5,540,734
U.S. Pat. No. 5,735,505
U.S. Pat. No. 5,752,911
U.S. Pat. No. 5,840,069
U.S. Pat. No. 6,016,449
U.S. Pat. No. 6,036,459
U.S. Pat. No. 6,051,017
U.S. Pat. No. 6,132,361
U.S. Pat. No. 6,176,242
U.S. Pat. No. 6,251,669
U.S. Pat. No. 6,425,852
U.S. Pat. No. 6,567,696
U.S. Pat. No. 6,592,509
U.S. Pat. No. 6,609,031
U.S. Pat. No. 6,620,151
U.S. Pat. No. 6,629,973
U.S. Pat. No. 6,735,474
U.S. Pat. No. 6,735,475
U.S. Pat. No. 6,782,292
U.S. Application No. 60/528,604
U.S. Application No. 60/528,689

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

We claim:

1. A method of treating a mood disorder or anxiety disorder, comprising:
    surgically implanting an electrode in communication with a predetermined site selected from the group consisting of inferior thalamic peduncle and reticular thalamic nucleus;
    coupling the electrode to a pulse generating source; and
    treating the mood disorder or the anxiety disorder by generating an electrical signal with the pulse generating source wherein said signal electrically stimulates the predetermined site.

2. The method of claim 1 further comprising:
surgically implanting a catheter having a proximal end coupled to a pump and a discharge portion for infusing a dosage of a pharmaceutical, wherein after implantation the discharge portion of the catheter is in communication with a predetermined site selected from the group consisting of inferior thalamic peduncle and reticular thalamic nucleus; and
operating the pump to discharge the pharmaceutical through the discharge portion of the catheter into the predetermined site thereby chemically stimulating the predetermined site and treating the mood disorder and/or anxiety disorder.

3. The method of claim 2, wherein chemical stimulation of the predetermined site results in modulation of neuronal activity.

4. The method of claim 2, wherein the pharmaceutical is selected from the group consisting of an inhibitory neurotransmitter agonist, an excitatory neurotransmitter antagonist, an agent that increases the level of an inhibitory neurotransmitter, an agent that decrease the level of an excitatory neurotransmitter, and a local anesthetic agent.

5. The method of claim 1, wherein the mood disorder is selected from the group consisting of major depressive disorder, bipolar disorder, and dysthymic disorder.

6. The method of claim 5, wherein the mood disorder is major depressive disorder.

7. The method of claim 1, wherein the anxiety disorder is selected from the group consisting of panic disorder, post-traumatic stress disorder, obsessive-compulsive disorder and phobic disorder.

8. The method of claim 7, wherein the anxiety disorder is obsessive-compulsive disorder.

9. The method of claim 1, wherein electrical stimulation of the predetermined site results in modulation of neuronal activity.

10. The method of claim 1, wherein the predetermined site is the inferior thalamic peduncle.

11. The method of claim 1, wherein the predetermined site is the reticular thalamic nucleus.

* * * * *